(12) United States Patent
Warf, Jr. et al.

(10) Patent No.: US 8,318,231 B2
(45) Date of Patent: Nov. 27, 2012

(54) OXIDATION METHOD AND COMPOSITIONS THEREFOR

(75) Inventors: C. Cayce Warf, Jr., Woodinville, WA (US); Nahed M. Kotrola, Searcy, AK (US)

(73) Assignee: Ecolab USA Inc., St. Paul, MN (US)

( * ) Notice: Subject to any disclaimer, the term of this patent is extended or adjusted under 35 U.S.C. 154(b) by 120 days.

(21) Appl. No.: 12/726,155

(22) Filed: Mar. 17, 2010

(65) Prior Publication Data

US 2010/0227004 A1 Sep. 9, 2010

Related U.S. Application Data

(63) Continuation of application No. 11/209,116, filed on Aug. 22, 2005, now abandoned.

(51) Int. Cl.
*C11B 5/00* (2006.01)
*A23L 3/00* (2006.01)

(52) U.S. Cl. .................. 426/534; 426/531; 426/535

(58) Field of Classification Search .................. 426/531, 426/532, 534, 535, 541, 641, 652, 654
See application file for complete search history.

(56) References Cited

U.S. PATENT DOCUMENTS

| | | | |
|---|---|---|---|
| 4,051,058 A | 9/1977 | Bowing |
| 4,051,059 A | 9/1977 | Bowing |
| 4,547,381 A | 10/1985 | Mason |
| 5,200,189 A | 4/1993 | Oakes |
| 5,314,687 A | 5/1994 | Oakes |
| 5,389,390 A | 2/1995 | Kross |
| 5,407,656 A | 4/1995 | Roozdar |
| 5,409,713 A | 4/1995 | Lokkesmoe |
| 5,437,868 A | 8/1995 | Oakes |
| 5,489,434 A | 2/1996 | Oakes |
| 5,674,538 A | 10/1997 | Lokkesmoe |
| 5,687,724 A | 11/1997 | Jewett |
| 5,718,910 A | 2/1998 | Oakes |
| RE36,064 E | 1/1999 | Davidson |
| 6,010,729 A | 1/2000 | Gutzmann |
| 6,063,425 A | 5/2000 | Kross |
| 6,102,286 A | 8/2000 | Hammond |
| 6,113,963 A | 9/2000 | Gutzmann |
| 6,183,807 B1 | 2/2001 | Gutzmann |
| 6,197,215 B1 | 3/2001 | Pitochelli |
| 6,383,541 B1 | 5/2002 | Danner |
| 6,514,556 B2 | 2/2003 | Hilgren |
| 6,524,624 B1 | 2/2003 | Morelli |
| 6,545,047 B2 | 4/2003 | Gutzmann |
| 6,699,510 B2 | 3/2004 | McSherry |
| 6,764,661 B1 | 7/2004 | Girard |
| 2003/0180384 A1 | 9/2003 | Koermer |
| 2005/0155936 A1 | 7/2005 | Martin |

FOREIGN PATENT DOCUMENTS

| | | |
|---|---|---|
| WO | WO0013506 | 3/2000 |
| WO | WO0230203 | 4/2002 |
| WO | WO03080506 | 10/2003 |
| WO | WO2004032979 | 4/2004 |

OTHER PUBLICATIONS

Food and Drug Administration, HHS, *21 CFR Ch. 1* (Apr. 2005 Edition), §173 pgs. 140-142, 3 pgs.
Food Standards, "*Final Assessment Report, Application A476, Acidified Sodium Chlorite as a Processing Aid*", 12/03, Oct. 8, 2003, 27 pgs.
Heintz, Sam, "*Waste Water from Poultry Operations*", Southern Arkansas University, http://hmtri.org/ncpete/2004pete/ww_from_poultry_oper04.ppt#280.25,Process Plant Waste, 26 pgs.
Kiepper, Brian Harry, "*Characterization of Poultry Processing Operations, Wastewater Generation, and Wastewater Treatment Using Mail Survey and Nutrient Discharge Monitoring Methods*", http://www.engr.uga.edu/service/outreach/kiepper_brian_h_200308 ms.pdf, 2003, 140 pgs.
*Standard Practice for Coagulation-Flocculation Jar Test of Water*, Designation: D 2035-80 (Reapproved 2003), 4 pgs.
Sungwaraporn, Yuwares, "*Lipid and Protein Quality of Poultry By-Products Preserved by Phosphoric Acid Stabilization*", http://ww.lib.ncsu.edu/theses/available/etd-11302004-181923/unrestricted/etd.pdf, 2004, 221 pgs.

*Primary Examiner* — Leslie Wong
(74) *Attorney, Agent, or Firm* — Andrew D. Sorensen; Laura C. DiLorenzo

(57) ABSTRACT

The present invention generally relates to an improved two-part oxidizing system, as well as oxidizing compositions and methods for making and using the same, and in a particular embodiment to a two-part oxidizing system that, when mixed, yields an oxidizing composition. The two-part oxidizing system includes a metal chlorite first part, and an acid second part where the acid is sodium acid sulfate or a derivative thereof.

18 Claims, 9 Drawing Sheets

OXIDATION METHOD AND COMPOSITIONS THEREFOR

CROSS REFERENCE TO RELATED APPLICATIONS

This application is a continuation of U.S. patent application Ser. No. 11/209,116, filed Aug. 22, 2005, now abandoned, published as US2007/0042094, the entire disclosure of which is incorporated herein by reference in its entirety.

FIELD OF THE INVENTION

The present invention generally relates to an improved two-part oxidizing system, as well as oxidizing compositions and methods for making and using the same, and in a particular embodiment to a two-part oxidizing system that, when mixed, yields an oxidizing composition. The two-part oxidizing system includes a metal chlorite first part, and an acid second part where the acid is sodium acid sulfate or a chemical moiety that provides the bisulfate ion in situ.

BACKGROUND OF THE INVENTION

Many diseases arise from the growth and spread of microorganisms that can affect all aspects of life, from human health, to animal health, to food and water safety, to the safety of the environments we live in. Oxidizers and disinfectants have found wide spread application in all these areas. Hospitals perform rigorous programs to disinfect and sterilize their environments. Consumer homes are replete with disinfectant hand cleaners, sprays, hard surface cleaners, disinfectant wipes, and fruit and vegetable washes. Disinfectants are widely used on farms where the difference between healthy and sick animals can mean the difference between profitability and loss.

Acidified chlorite (AC) oxidizers are commonly formed from two-part products having a first or base part containing a chlorite (such as sodium chlorite) and a second or activated part containing an acid activator. The AC oxidizer is formed upon mixing the first and second parts, and typically only in amounts sufficient for a given use period. Depending on the desired characteristics and/or intended use of the AC oxidizer, either the first or second part, or both parts, may contain one or more additional functional ingredients. Also, depending on the two-part system, the AC oxidizing composition may be formed by simply mixing the first and second parts, often in approximately equal volumes, or may involve some additional dilution step before or after mixing.

Acidified chlorite compositions may be generated by combining a source of chlorite ions (i.e., $ClO_2^-$), typically in the form of a metal salt such as sodium chlorite, with an acid activator. Such compositions are effective oxidizers due to the generation of antimicrobial oxidants, particularly chlorous acid (i.e., $HClO_2$). Chlorous acid is formed very rapidly upon acidification of chlorite in an equilibrium process governed by the solution pH.

AC compositions differ significantly from compositions that are designed to produce chlorine dioxide. Chlorine dioxide compositions contain high amounts of chlorite and acid which is typically a mineral acid such as hydrochloric acid. The lower the pH of the composition, the faster the formation of chlorine dioxide. These reactions are described in detail in U.S. Pat. Nos. Re 36,064 and 6,063,425 which are incorporated by reference herein in their entirety.

Previously, a preferred acid activator for AC compositions has been an organic acid and preferably citric acid because the pH of organic acids is typically higher than the pH of mineral acids therefore allowing for the controlled formation of chlorous acid without the chlorous acid rapidly degrading to chlorine dioxide. In addition, citric acid is a food additive or GRAS (generally recognized as safe) acid meaning that it can be applied directly to food and food contact surfaces without being rinsed off. However, organic acids, and citric acid in particular, have several undesirable side effects.

AC compositions are used as an antimicrobial on food products and in particular poultry products. Spent water in poultry plants has to be treated to remove impurities from the water before being reused or being sent outside the plant. Fats and oils from poultry are some of the components of plant wastewater that need to be removed. One method of removing fats and oils from plant wastewater is using dissolved air floatation (DAF) which floats the fats and oils in solution to the top of the water where they can be skimmed off the surface and either disposed of or used. Fats and oils typically have charges associated with them which make them repel other fat and oil particles, negatively impacting coagulation and/or coalescing. When using DAF a coagulant may be used to neutralize charges on the fats and oils and make them more likely to form larger globules that are more likely to float to the top. Typical coagulants include metal salts such as $FeCl_2$, $FeCl_3$, $FeSO_4$, or $Al_2(SO_4)_3$. In addition to using a coagulant, a flocculant may also be used after the coagulation step. Flocculants are typically polymers that are designed to bridge fat and oil particles in solution together to form larger particles that are more likely to float to the top. Most of the wastewater treatment costs in food processing facilities are associated with adding coagulants and flocculants to the water.

Citric acid is a sequestrant and interferes with the ability of the coagulant to work effectively because the cations of the coagulant (that is the metal ions) are tied up to the citric acid and is no longer free to neutralize the surface charges of the fats and oils in the water. This has many negative side effects. More coagulant must be added to neutralize the fats and oils which increases the operation costs of a plant. The combination of citric acid and coagulant forms a solid which must be removed from the water and disposed of. The process quality goes down and the manpower needed to make the process work increases which means increased costs for the plant. More flocculant must be added which also increases the operation costs for the plant.

The solids may be disposed of in several ways. For example, the solids may be disposed of by collecting them and applying them to the land. However, approval from local authorities must be obtained first. The solids may be incorporated into feed or feed additives for animals. However, sometimes the solids contain too many metal cations to be used as a feed additive. Finally, the solids may be placed in a landfill. However, depositing material in landfills is environmentally undesirable and not all states allow this practice.

In addition to increasing the solids, citric acid usage increases the turbidity of the wastewater. High turbidity or high solids in the wastewater is undesirable because it creates places for bacteria to grow in the water. Further high turbidity increases the COD or chemical oxygen demand of the wastewater which is undesirable. COD is a measure of the level of organics in the water. The higher the COD, the more organics are present in the water. Organics are undesirable because they provide a food for bacteria to grow. Further, wastewater discharge rules limit the quantity of organics that can be in the effluent wastewater. Finally, high turbidity or high solids in water is aesthetically undesirable.

Another undesirable side effect of citric acid on wastewater treatment is the diminished removal of phosphorous from the wastewater. Plants use phosphorous compounds (generally in the form of phosphates) in several places including cleaning solutions, and meat tenderizers/stabilizers in poultry plants. Phosphorous must be removed in wastewater treatment before being released into the environment because phosphorous contributes to the eutrification, or algae growth, in wastewater or the body of water that the wastewater is released into. Consequently, the phosphorous must be removed or the plant has to pay to have it be removed or is fined if the phosphorous level is not low enough. During the wastewater treatment process, the phosphorous is precipitated out of solution and can then be removed. However the citric acid causes the phosphorous to remain in solution in the wastewater, which makes it more difficult to remove during the wastewater treatment process.

After the water is treated using DAF, the water goes to biological treatment to remove organics from the water. The wastewater treatment plant may be either a publicly owned treatment works (POTW) facility or part of the food processing plant facility. Biological treatment uses aerobic and anaerobic bacteria to remove organics from the water prior to discharge into a receiving stream. Regulatory agencies look at the health of certain sensitive organisms including Daphnia and fat-head minnows in the receiving stream as an indication of the quality of the water treatment process. Because Daphnia are sensitive to the ionic strength of the water, controlling the number of ions in the water is important to keeping them healthy. Citric acid based acidified sodium chlorite compositions add a significant amount of ions to the water in a typical poultry plant (~10,000 to 14,000 ppm ions), most of which come from the citric acid. This process constitutes 1-2% of the total wastewater discharge of a typical poultry slaughter facility. With this dilution, the resulting contribution of 100 to 280 ppm of ions may negatively impact the health of the biota in the receiving streams.

In recent years, high energy costs, high water costs, high wastewater disposal costs, high solid waste disposal costs, and high raw material costs have become a reality for plant operators. Additionally, awareness continues to increase on protecting the environment by recycling instead of depositing materials in landfills, using less water, using less energy, protecting resources, and generally negatively impacting the environment as little as possible. Compositions and processes like AC compositions using citric acid require more energy and raw materials to work effectively and to remove impurities and pollutants from the wastewater, and they generate more solid byproducts that need to be disposed of. A need exists for more environmentally friendly, or "green" AC compositions that work just as well antimicrobially as organic acid based AC compositions, but without the negative environmental side effects.

In addition to negative side effects on wastewater treatment, the use of organic acids, and citric acid in particular, have several other undesirable characteristics. For example, because citric acid is a sequestrant the citric acid negatively reacts with water hardness ions such as calcium and magnesium if the plant is using hard water. The result is that significantly more citric acid must be used in order to generate a sufficient amount of chlorous acid which increases costs for the plant. Also, citric acid has been observed to discolor chicken wings which creates an undesirable product for the consumer. Further, the pH of citric acid levels out between pH 2 to 3 in that if more citric acid is added, the pH does not change significantly. This is due in part to the buffering capabilities of citric acid. If a lower pH is desired, a significant amount of citric acid must be added in order to lower the pH below its buffering range. Finally, because citric acid is an organic acid, it can potentially leave behind carbon residues that bacteria can grow on which is undesirable.

It is against this background that the present invention has been made.

SUMMARY

Surprisingly, it has been discovered that sodium acid sulfate or a moiety which delivers the bisulfate ion ($HSO_4^-$) in solution is just as effective an acid activator as citric acid at forming metastable chlorous acid compositions with many of the same advantages of citric acid but without the disadvantages described above. This is extremely unexpected because sodium acid sulfate is a mineral acid which has been traditionally associated with the rapid formation of chlorine dioxide. First, sodium acid sulfate does not have negative effects on wastewater treatment or the environment. Specifically, sodium acid sulfate is not a sequestrant so it does not negatively react with a metal-containing coagulant. Further, less sodium acid sulfate needs to be used to generate chlorous acid so fewer ions are present in solution to harm the bacteria in a water treatment plant or the biota in the receiving stream. Second, sodium acid sulfate is available as a GRAS (generally recognized as safe), or food additive acid, which means it can be applied directly to a food product as an antimicrobial composition. Third, sodium acid sulfate based AC compositions do not discolor chicken wings to the extent that citric acid based AC compositions do. Fourth, sodium acid sulfate is less sensitive to water hardness ions so less sodium acid sulfate is needed than citric acid if a plant is using hard water. Fifth, the pH of sodium acid sulfate does not level out the way that the pH of the buffering citric acid does, which allows for greater range of control and flexibility over the pH by a formulator. Sixth, sodium acid sulfate is a mineral acid which means that it does not leave behind carbon residues for bacteria to grow on. Finally, sodium acid sulfate is more readily available than citric acid and less expensive.

In some embodiments, the present invention relates to a two-part oxidizing system having a metal chlorite first part and a sodium acid sulfate activator second part.

In some embodiments, the present invention relates to a two-part oxidizing system that, when combined, the metal chlorite first part and the sodium acid sulfate activator second part form an oxidizing composition having a utility over a wide range of applications. These oxidizing compositions can be applied to any surface material or fluid that will benefit from being oxidized or disinfected.

In some embodiments, the present invention relates to an environmentally friendly or "green" acidified chlorite composition that the consumptions of fewer water treatment chemicals in the treatment of wastewater and less energy than acidified chlorite compositions formed using an organic acid and forms fewer solids that need to be disposed of. In some embodiments, the present invention relates to an acidified chlorite composition that produces fewer ions in the wastewater than acidified chlorite compositions formed using an organic acid.

In some embodiments, the present invention relates to an acidified chlorite composition that does not negatively impact the turbidity of the wastewater or the removal of phosphorous from the wastewater as is the case with citric acid based AC compositions.

In some embodiments, the present invention relates to methods of oxidizing surfaces.

In some embodiments, the present invention relates to methods of disinfecting surfaces.

In some embodiments, the present invention relates to methods of oxidizing unwanted components in fluids.

In some embodiments, the present invention relates to methods of disinfecting fluids.

These and other aspects of the invention will be evident upon reference to the following detailed description of the invention.

DETAILED DESCRIPTION OF THE INVENTION

Definitions

Figure 1:
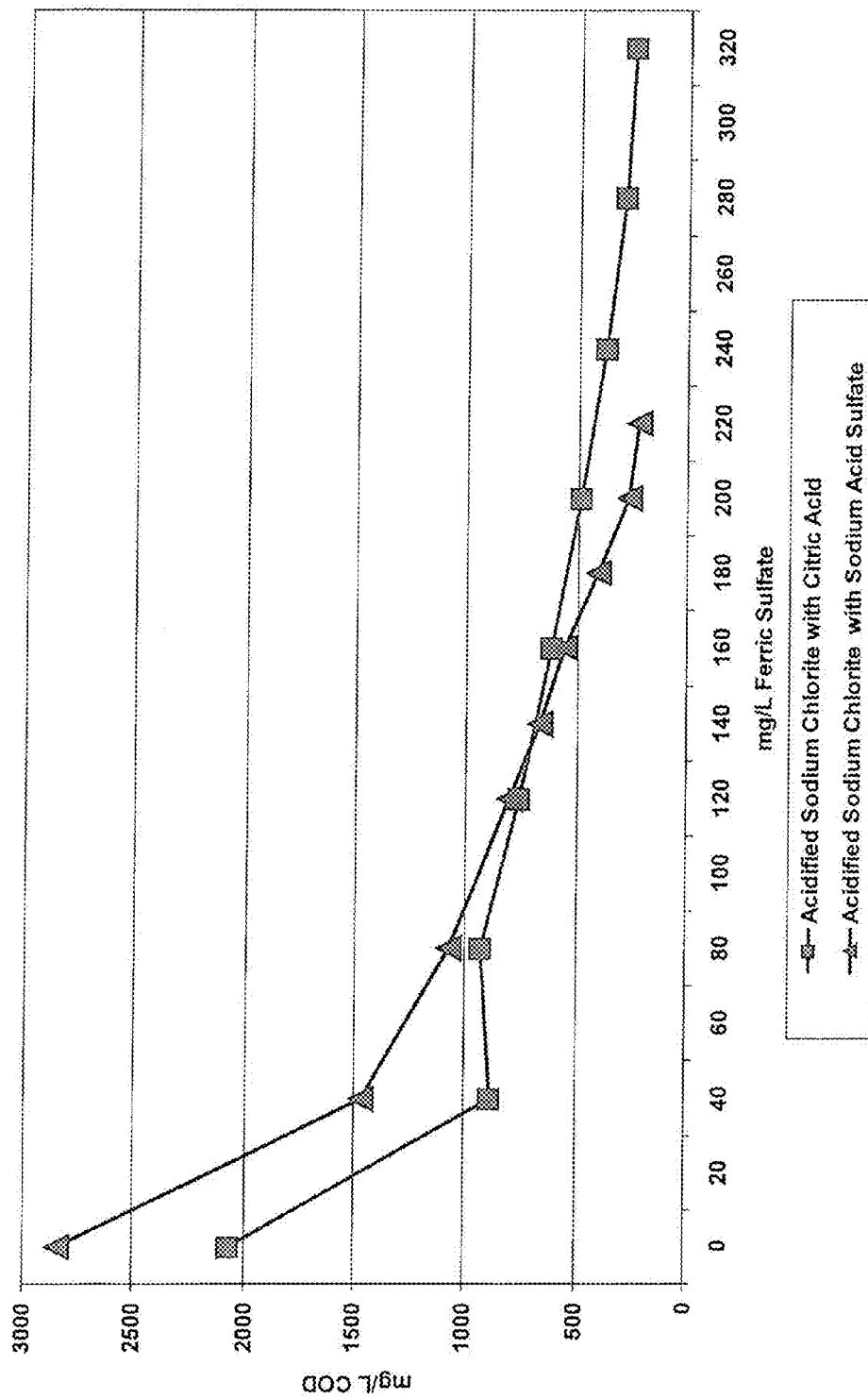
FIGS. 1 and 2 are graphical depictions of the impact of acidified sodium chlorite compositions made with citric acid and sodium acid sulfate on the chemical oxygen demand.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100. Concentrations given in ppm, or parts per million, refer to the concentration of a substance as the weight of that substance divided by the weight of the total composition and multiplied by 1,000,000. For dilute aqueous solutions, ppm is roughly equivalent to milligrams/liter.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the terms "antimicrobial" and "biocide" in this application does not mean that any resulting products are approved for use as an antimicrobial agent or biocide.

The term "oxidizer" refers to a composition that results in the oxidation of another substance. In the process, the oxidizer is reduced, i.e., one or more atoms in the oxidizer experience a lowering in its oxidation number. One or more atom in the molecule species that is oxidized experiences an increase in its oxidation number. For in the oxidation of four iron(II) ions to four iron(III) ions by one molecule of chlorous acid (wherein the chlorine atom has an oxidation state of +3) to produce chloride ion with an oxidation state of −1, the four oxidized iron ions loses one electron per atom, while the chlorine atom gains 4 electrons. An oxidizer includes compositions that act as bleaching agents. An oxidizer also includes compositions that act as disinfectants.

The term "disinfectant" refers to a composition that reduces the number of microorganisms on a surface or in a fluid. The term "disinfectant" also refers to a composition that kills microorganisms on a surface or in a fluid. Fluid encompasses both liquids and gases. Microorganisms include but are not limited to bacteria, viruses, fungi, and the like.

Compositions

As noted above, in one embodiment a two-part oxidizing system is disclosed comprising a first part and a second part adapted to be combined to yield an aqueous oxidizing composition. The first part includes a chlorite and the second part includes an acid and specifically sodium acid sulfate or a moiety providing the bisulfate ion in solution.

Acidified chlorite compositions may be generated by combining chlorite (i.e., $ClO_2^-$), typically in the form of a metal salt such as sodium chlorite, with an acid activator. Such compositions are effective oxidizers and disinfectants due to the generation of antimicrobial oxidants, particularly chlorous acid (i.e., $HClO_2$). Chlorous acid is formed very rapidly upon acidification of chlorite in an equilibrium process governed by the solution pH.

The present invention can be distinguished in several ways from compositions designed to form chlorine dioxide, the most notable distinction being that the present invention forms relatively low amounts of chlorous acid in comparison to those compositions designed to form chlorine dioxide. When forming chlorine dioxide compositions, high levels of chlorous acid are required in order to form high levels of chlorine dioxide. In contrast, the present invention forms roughly 10 to 10,000 ppm chlorous acid, 10 to 2,000 ppm chlorous acid, and 10 to 1,500 ppm chlorous acid.

The first and second parts may both be in the form of an aqueous composition, emulsion, microemulsion, cream or gel, or one or both may be in a concentrated, non-aqueous or solid form, such as a powder, solid block, tablet, pellet, or prin. For example, the first and second parts may be aqueous compositions or gels to be mixed in approximately equal volumes to form the disinfecting composition, or may be concentrates or solids to be diluted by or dissolved in water, and then mixed to yield the disinfecting composition. Alternatively, the first and/or second parts may be in a non-aqueous or solid form (such as a powder or tablet) to be mixed with or dissolved in water prior to combination. To avoid excessive generation of chlorine dioxide which may occur upon combination of concentrated forms, it is preferable to mix the first and second parts after the parts are diluted with or dissolved in water.

Chlorite

The chlorite of the first part is typically an alkali or alkaline earth metal chlorite, such as potassium or sodium chlorite, and more typically sodium chlorite. The chlorite is present in the first part in an amount such that, when combined with the second part, it is present within the composition at a concentration ranging from about 0.001% to about 2.0% by weight, from about 0.01% to about 1.0% by weight, from about 0.02% to about 0.3% by weight, and from about 0.02% to about 0.12%.

Sodium Acid Sulfate

The acid of the second part is sodium acid sulfate or a moiety which provides the bilsulfate ion ($HSO_4^-$) in solution. Sodium acid sulfate ($NaHSO_4$) is also known as sodium bisulfate. Some non-limiting examples of moieties capable of producing the bilsulfate ion in solution include compositions of sodium acid sulfate where the sodium ion of the sodium acid sulfate is replaced with either a metal ion having a formal charge of +1 or +2 such as potassium hydrogen sulfate ($KHSO_4$), or cesium hydrogen sulfate ($CsHSO_4$).

Sodium acid sulfate and the bisulfate ion producing moieties have been surprisingly found to be a preferred acid activator when forming acidified chlorite compositions because they have the advantages of an organic acid in terms of food additive or GRAS status and target pH range which can range below that attainable with the organic acids without any of the disadvantages previously discussed.

Sodium acid sulfate obtained status as a GRAS additive in 1998. Prior to obtaining GRAS status, sodium acid sulfate was not a viable option for forming chlorous acid, particularly for applications on food or food contact surfaces. After obtaining GRAS status, sodium acid sulfate was still not a likely candidate for forming chlorous acid because it is a mineral acid and mineral acids have traditionally been associated with rapidly forming chlorine dioxide. However, sodium acid sulfate has surprisingly and unexpectedly proven to be a preferred candidate for forming chlorous acid because its pKa of ~2.0 extends the achievable level of chlorous acid (relative to the total chlorite ion concentration) to 50% at a pH of 2.0 or even to 74% at a pH of 1.5.

Other mineral acids such as hydrochloric acid, have pKas that are too low to be useful in forming chlorous acid because at high levels they rapidly covert to chlorine dioxide, and at low levels (i.e., levels low enough to form chlorous acid) they are too difficult to dispense consistently and control because the levels are so small.

In addition to having several advantages for forming chlorous acid, sodium acid sulfate does not have many of the disadvantages that organic acids have.

For example, organic acids have negative side effects in wastewater treatment which have been previously discussed. Sodium acid sulfate does not negatively impact wastewater treatment, both in terms of the treatment chemicals and in terms of the ionic strength of the spent process water. Table 1 describes two AC compositions, one using citric acid and one using sodium acid sulfate. These formulas are intended to be exemplary only and not limiting the invention.

TABLE 1

| Exemplary AC Compositions | |
|---|---|
| Citric Acid Formula | Sodium Acid Sulfate Formula |
| 1000 ppm Sodium Chlorite<br>6000 ppm Citric Acid<br>pH = 2.5 | 1000 ppm Sodium Chlorite<br>700-950 ppm Sodium Acid Sulfate<br>pH = 2.5 |

Table 1 shows that considerably more citric acid, more than six times the amount of sodium acid sulfate, must be added to the citric acid formula in order for the pH to drop to 2.5. Because citric acid has sequestering capabilities, this large amount of citric acid interferes with metal salt coagulants forcing a plant to use more coagulant and flocculant. The citric acid also increases the number of solids that have to be removed from the water and later disposed of.

Additionally, the high level of citric acid significantly increases the ion concentration in the water, which can adversely affect the health of bacteria used in the water treatment process as well as the biota in the receiving stream. In the citric acid formula in Table 1, the sodium chlorite creates 2000 ppm ions from the $Na^+$ and $Cl^-$ ions. The citric acid creates 12,000 ppm ions from the $H^+$ and citrate ions. This creates a total of 14,000 ppm of ions. Some of these ions are tied up with the coagulant or in the form of chlorous acid. However, a large portion will remain as ions. Comparatively, the sodium acid sulfate composition will have 2,000 ions from the sodium chlorite in the form of $Na^+$ and $Cl^-$ ions, and 1400-1900 ppm of ions from the sodium acid sulfate in the form of $H^+$ and bisulfate ions. This is significantly lower than the ion concentration of the citric acid formula and therefore more preferable for the health of the bacteria used in wastewater treatment as well as the health of the biota (such as *Daphnia* spp) in the receiving stream.

Because citric acid is a sequestrant, the citric acid negatively reacts with water hardness ions such as calcium and magnesium if the plant is using hard water. The result is that significantly more citric acid must be used in order to generate a sufficient amount of chlorous acid, which increases costs for the plant. In contrast, the sodium acid sulfate does not react with water hardness ions to the same extent. If a plant is using hard water, the amount of sodium acid sulfate that needs to be added to generate a desired amount of chlorous acid does not need to be adjusted as strongly as if the acid is citric acid. This creates more certainty when calculating the desired amount of sodium acid sulfate because the type of water being used does impact as strongly as if one is using an organic acid such as citric acid.

Figure 9:
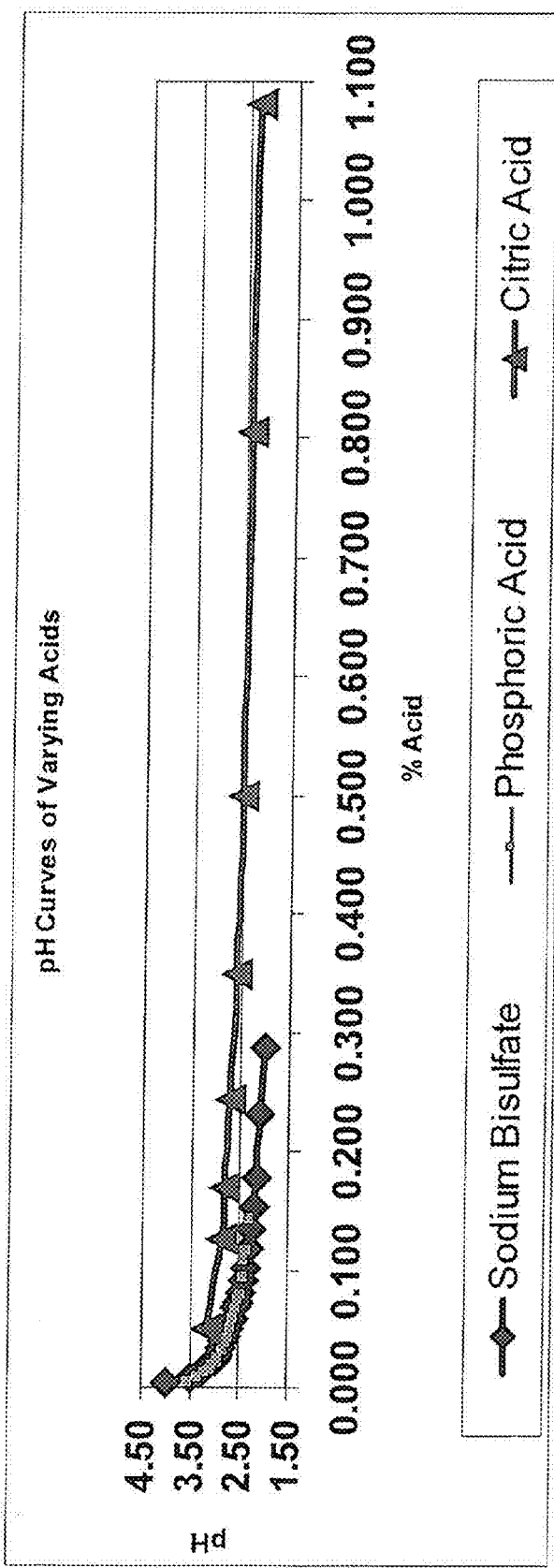
FIG. 9 is a graphical depiction of the pH curves of various acids.

FIG. 9 shows how the pH of citric acid levels out between pH 2 and 3 in that if more citric acid is added, the pH does not change significantly. In contrast, the pH of sodium acid sulfate continues to decrease if more sodium acid sulfate is added to a composition. This is advantageous because it allows for greater pH control and flexibility without having to add large amounts of acid in order to create a change in pH. By controlling the pH of the composition, a formulator can control the amount of chlorous acid generated and the conversion rate to chlorine dioxide. In some instances, it is desirable to have a composition that forms chlorous acid without rapidly converting to chlorine dioxide. However, in other instances, such as rapid disinfecting compositions, it is desirable to have a composition that generates a high amount of chlorous acid and is rapidly converted to chlorine dioxide. Sodium acid sulfate allows a formulator to have this kind of flexibility, without having to add large amounts of acid, which is more cost effective for a customer.

In addition to the above described advantages, sodium acid sulfate also does not contribute to discoloration of poultry products to the extent that citric acid AC compositions does, nor does it leave behind a carbon residue for bacteria to grow on.

The sodium acid sulfate or sodium acid sulfate derivative is present in the second part in an amount such that, when combined with the first part, it is present in the oxidizing composition at a concentration ranging from about 0.001% to about 2.0% by weight, from about 0.01% to about 1.0% by weight, from about 0.02% to about 0.3% by weight, and from about 0.02% to about 0.12% by weight. Alternatively, the amount of acid in the second part may be characterized by the pH of the final oxidizing composition. In this regard, the acid is present in the second part in an amount such that, when combined with the first part, the pH of the oxidizing composition is from about 1.0 to about 4.0, from about 1.5 to about 3.0, from about 1.9 to about 2.7, and from about 2.0 to about 2.6.

Additional Functional Ingredients

Various additional functional ingredients may also be present in the first part, the second part, or both first and second parts of the two-part system. Alternatively, some or all of the additional functional ingredients may be in a third part, or individually added to the composition. These ingredients may be used to enhance the effectiveness of the composition, or impart an additional benefit. Such ingredients include (but are not limited to) chelating agents, additional acids, hydrotropes, thickening or gelling agents, additional antimicrobial agents, carriers, wetting or defoaming agents, foaming agents, builders, textural modifiers, film-forming agents, rheology modifiers, surfactants, flavoring aids, colorants, fragrances, skin conditioning agents, and mixtures thereof. With all of these additional functional ingredients, preferred ingredients are those that do not render the AC composition substantially ineffective. A person skilled in the art will be able to select the various ingredients so as to not render the AC compositions substantially ineffective.

Additional Acids

The composition may optionally include acids in addition to the sodium acid sulfate. For example, the composition may include an organic acid. Some non-limiting examples of organic acids include glycolic acid, citric acid, lactic acid, formic acid, acetic acid, propionic acid, butyric acid, valeric acid, caproic acid, gluconic acid, itaconic acid, trichloroacetic acid, urea hydrochloride, benzoic acid, oxalic acid, malonic acid, succinic acid, glutaric acid, maleic acid, fumaric acid, adipic acid, terephthalic acid, and the like.

Antimicrobial Agents

The composition may optionally include an additional antimicrobial agent. Some non-limiting examples of antimicrobial agents that may be used include fatty acids, C1-C12 dicarboxylic acids, percarboxylic acids, halogen compositions or interhalogens thereof, a halogen donor composition, chlorine dioxide, acidified sodium chlorite, ozone, a quaternary ammonium compound, an acid-anionic organic sulfonate or sulfate, a protonated carboxylic acid, or mixtures thereof. Some non-limiting examples of percarboxylic acids include: C1-C10 percarboxylic acids, diperoxyglutaric acid, diperoxyadipic acid, diperoxysuccinic acid, diperoxysuberic acid, diperoxymalonic acid, peroxylactic acid, peroxyglycolic acid, peroxyoxalic acid, peroxypyruvic acid, and mixtures thereof. Some non-limiting examples of halogen compounds and interhalogens thereof include: $Cl_2$, $Br_2$, $I_2$, $IC_1$, IBr, ClBr, $ICl_2^-$, $Mr_2$, and mixtures thereof. Non-limiting examples of halogen donor compositions include: HOCl, HOI, HOBr, and the salts thereof; N-iodo, N-bromo, or N-chloro compounds; and N-bromosuccinamide, chloroisocyanuric acid, or 2-N-sodium-N-chloro-p-toluenesulfonamide. A non-limiting example of chlorine dioxide compositions includes chlorine dioxide generated from conventional chemical generators such as those sold by Prominent™ or preferably generated electrochemically using Halox™ generators. A non-limiting example of ozone includes ozone generated electrochemically via high voltage discharge in oxygen. Non-limiting examples of quaternary ammonium compounds include: didecyldimethylammonium chloride, dioctyldimethylammonium chloride, octyldecyldimethylammonium chloride, alkyldimethylbenzylammonium chloride, and mixtures thereof. Non-limiting examples of acid-anionic organic sulfonates and sulfates include: acidic solutions of linear benzylsulfonic acid and sulfonated oleic acid. Non-limiting examples of protonated carboxylic acids include solutions with a pH less than 5 of one or more C1-C20 carboxylic acids. See U.S. Pat. Nos. 4,051,058, 4,051,059, 5,200,189, 5,200,198, 5,489,434, 5,718,910, 5,314,687, 5,437,868 for further discussion on peracid chemistry and the formation of an antimicrobial agent formulation. These patents are incorporated herein by reference in their entirety.

Carriers

The composition may optionally include a carrier. The carrier provides a medium which dissolves, suspends, or carries the other components of the composition. For example, the carrier can provide a medium for solubilization and production of the composition and for forming an equilibrium mixture. The carrier also functions to deliver and wet the composition on the intended surface or medium. To this end, the carrier may contain any component or components that can facilitate these functions.

Generally, the carrier includes primarily water which is an excellent solubilizer and medium for reaction and equilibrium. The carrier can include or be primarily an organic solvent, such as simple alkyl alcohols, e.g., ethanol, isopropanol, n-propanol, and the like. Polyols are also useful carriers, including propylene glycol, polyethyleneglycol, glycerol, sorbitol, and the like. Any of these compounds may be used singly or in combination with other organic or inorganic constituents or, in combination with water or in mixtures thereof.

Chelating Agents

The composition may optionally include a polyvalent metal complexing or chelating agent that aids in reducing the harmful effects of hardness components and service water and improves product stability. The typically harmful effects of calcium, magnesium, iron, manganese, etc., ions present in service water can interfere with the composition. The chelating agent or sequestering agent can effectively complex and remove such ions from inappropriate interaction with active ingredients thus increasing performance.

Both organic and inorganic chelating agents may be used. Inorganic chelating agents include such compounds as sodium tripolyphosphate and other higher linear and cyclic polyphosphate species. Organic chelating agents include both polymeric and small molecule chelating agents. Polymeric chelating agents commonly comprise polyanionic compositions such as polyacrylic acid compounds. Amino phosphates and phosphonates are also suitable for use as chelating agents in the compositions of the invention and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms.

Chelating agents for use in this invention include improved food additive chelating agents such as disodium salts of ethylene diamine tetraacetic acid or the well known phosphonates sold in the form of DEQUEST® materials, for example, 1-hydroxyethylidene-1,1-diphosphonic acid, etc. The phosphonic acid may also comprise a low molecular weight phosphonopolycarboxylic acid such as one having about 2-4 carboxylic acid moieties and about 1-3 phosphonic acid groups. Such acids include 1-phosphono-1-methylsuccinic acid, phosphonosuccinic acid and 2-phosphonobutane-1,2,4-tricarboxylic acid. Another organic phosphonic acid is ($CH_3C(PO_3H_2)_2OH$), available from Monsanto Industrial Chemicals Co., St. Louis, Mo., as DEQUEST® 2010, (which is a 58-62% aqueous solution; amino (tri(methylenephosphonic acid)]($N[CH_2PO_3H_2]_3$), available from Monsanto as DEQUEST® 2000, as a 50% aqueous solution; ethylenediamine [tetra(methylenephosphonic acid)] available from Monsanto as DEQUEST® 2041, as a 90% solid acid product; and 2-phosphonobutane-1,2,4-tricarboxylic acid available from Mobay Chemical Corporation, Inorganic Chemicals Division, Pittsburgh, Pa., as Bayhibit AM, as a 45-50% aqueous solution.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

Flavoring Aids, Fragrances, and Dyes

The composition may optionally include a flavoring aid for imparting a desired flavor to a food product or for masking an undesirable flavor. Some non-limiting examples of flavoring aids include marinades, tenderizers, and spices typically associated with food products and wintergreen or similar flavors associated with mouthwashes and the like.

The composition may also include a fragrance including natural and synthetic fragrances. Some non-limiting examples of fragrances include aldehydes, ketones, esters, essential oils, and the like.

Finally, the composition may include a dye. Some non-limiting examples of suitable dyes include FD&C and D&C dyes such as FD&C Blue No. 1, FD&C Blue No. 2, FD&C Green No. 3, FD&C Red No. 3, FD&C Red No. 40, FD&C Yellow No. 5, FD&C Yellow No. 6, Citrus Red No. 2, FD&C Red No. 4, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, D&C Yellow No. 8, D&C Yellow No. 10, D&C Yellow No. 11, and Ext. D&C Yellow No. 7, and dyes such as annatto extract, canthaxanthin, caramel, carrot oil, cochineal extract (carmine), corn endosperm oil, dehydrated beets (beet powder), dried algae meal, ferrous gluconate, fruit juice, grape color extract, grape skin extract, paprika, paprika oleoresin, riboflavin, saffron, synthetic iron oxide, tagetes meal and extract, titanium dioxide, toasted partially defatted cooked cottonseed flour, turmeric, termeric oleoresin, ultramarine blue, vegetable juice, cantaxanthin, beta carotene, chlorophyllin, and the like.

Film-Forming Agents, Rheology Modifiers, and Textual Modifiers

The composition of the invention may also contain one or more rheology modifiers, to enhance viscosity, or thicken and cause the aqueous treatment to cling to a surface. Clinging enables the composition to remain in contact with microorganisms for longer periods of time, promoting microbiological efficacy and resisting waste because of excessive dripping. The rheology modifier may be a film former or act cooperatively with a film-forming agent to form a barrier. Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SILS®) which have been fumed or precipitated to create particles with large surface to size ratios. Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are salts of complex anionic polysaccharides. Synthetic natural-based thickeners having application are cellulosic derivatives wherein the free hydroxyl groups on the linear anhydro-glucose polymers have been etherified or esterified to give a family of substances which dissolve in water and give viscous solutions. This group of materials includes the alkyl and hydroxyllalkycelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

In certain embodiments, a preferred aqueous thickening agents may be those which are extremely pseudoplastic (non-Newtonian, rapid relaxation), tend not to develop a rigid three-dimensional structure from interpolymer interactions, have a low or negligible viscoelastic character and possess a high gel strength. Such rheological properties are manifested for example in teat dip compositions which have a smooth flowing appearance, is easy to pour and apply onto the teat, coats uniformly without forming mucilage streamers as the applicator is withdrawn and remains firmly in place without significant sag. Examples of preferred rheology modifiers for teat dips and other applications are xanthan gum and the hydroxylalkylcelluloses.

Generally, the concentration of thickener used in the present invention will be dictated by the final composition and by the method of application. Spraying or misting requires a lower composition viscosity for easy and effective application of treatment.

Foaming Agents

The composition may optionally include a foaming agent or foaming surfactant. Foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides.

Hydrotropes

The composition may optionally include a hydrotrope coupler or solubilizer. Such materials can be used to ensure that the composition remains phase stable and in a single highly active aqueous form. Such hydrotrope solubilizers or couplers can be used at concentrations which maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include beta.-N-alkylaminopropionic acids, n-alkyl-beta-iminodipropionic acids, imidazoline carboxylates, n-alky-betaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10-80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula $R\text{-}(EO)_m\text{-}(PO)_n$ wherein m is an integer of about 2-10 and n is an integer from about 2-20. R can be any suitable radical such as a straight chain alkyl group having from about 6-20 carbon atoms.

Other useful nonionic surfactants of the invention include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO-PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant of the invention is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Skin Conditioning Agents

The composition may optionally include a skin conditioner such as an emollient, humectant, occlusive agent, or other moisturizer to provide moisturizing, skin softening, skin barrier maintenance, anti-irritation, or other skin health benefits. Some non-limiting examples of emollients include stearoxytrimethylsilane, alkyl benzoate, silicone oils, dimethicone, myristyl myristate, cetyl myristate, glyceryl dioleate, methyl laurate, PPG-9 laurate, octyl palmitate, lanolin, propylene glycol, glycerine, fatty acids, natural oils such as almond, mineral, canola, sesame, soybean, wheat germ, corn, peanut, and olive, isopropyl myristate, myristyl alcohol, aloe vera, hydrolyzed silk protein, stearyl alcohol, isopropyl palmitate, sorbitol, amino acid complexes, and polyethylene glycol. Some non-limiting examples of humectants include hydroxyethyl urea, agarose, arginine PCA, fructose, glucose, glutamic acid, glycerine, honey, lactose, maltose, propylene glycol, polyethylene glycol, sorbitol and mixtures thereof. Some non-limiting examples of occlusive agents include petrolatum, shea butter, alkyl dimethicones, avocado oil, balm mint oil, canola oil, cod liver oil, corn oil, methicone, mineral oil, olive oil, phenyl trimethicone, trimyristin, soybean oil, stearyl stearate, synthetic wax, or mixtures thereof. Some non-limiting examples of other moisturizers include cholesterol, cystine, hyaluronic acid, keratin, lecithin, egg yolk, glycine, PPG-12, panthenol, retinol, salicylic acid, vegetable oil, and mixtures thereof. Finally, some non-limiting examples of anti-irritants include bisabolol and panthenol.

Surfactants

The composition may optionally include a surfactant to help with detergency, surface wetting, and antimicrobial performance. Suitable surfactants include nonionic surfactants, anionic surfactants, cationic surfactants, amphoteric surfactants, amine oxides, and the like.

Anionic surfactants suitable for use in the present compositions and methods include n-octanesulfonate, available as NAS 8D from Ecolab Inc., n-octyl dimethylamine oxide, n-decyl dimethyl amine oxide, cocoa dimethylamine oxide, and the commonly available aromatic sulfonates such as the alkyl benzene sulfonates (e.g. dodecylbenzene sulfonate, cumene sulfonate, xylene sulfonates) or naphthalene sulfonates. Some preferred anionic surfactants include C6-C24 alkylbenzene sulfonates, C6-C24 olefin sulfonates, C6-C24 paraffin sulfonates, cumene sulfonate, xylene sulfonate, C6-C24 alkyl naphthalene sulfonates, C6-C24 alkyl or dialkyl diphenyl ether sulfonates or disulfonates, C4-C24 mono or dialkyl sulfosuccinates, sulfonated or sulfated fatty acids, C6-C24 alcohol sulfates (preferably C6-C12 alcohol sulfates), C6-C24 alcohol ether sulfates having 1 to about 20 ethylene oxide groups, and C4-C24 alkyl, aryl or alkaryl phosphate esters or their alkoxylated analogs having 1 to about 40 ethylene, propylene or butylene oxide units, or mixtures thereof.

Additional suitable surfactants include nonionic surfactants of C6-C24 alcohol ethoxylates (preferably $C_6$-$C_{14}$ alcohol ethoxylates) having 1 to about 20 ethylene oxide groups (preferably about 9 to about 20 ethylene oxide groups); C6-C24 alkylphenol ethoxylates (preferably C8-C10 alkylphenol ethoxylates) having 1 to about 100 ethylene oxide groups (preferably about 12 to about 20 ethylene oxide groups); C6-C24 alkylpolyglycosides (preferably C6-C20 alkylpolyglycosides) having 1 to about 20 glycoside groups (preferably about 9 to about 20 glycoside groups); C6-C24 fatty acid ester ethoxylates, propoxylates or glycerides; and C4-C24 mono or dialkanolamides.

Thickening or Gelling Agents

The composition may optionally include a thickener or gelling agent. Generally, thickeners which may be used in the present invention include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Generally, the concentration of thickener employed in the present compositions or methods will be dictated by the desired viscosity within the final composition.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Along these lines, surfactants, and especially nonionic surfactants, can also be useful in the present invention. Nonionic surfactants which can be useful in the present invention are those which include ethylene oxide moieties, propylene oxide moieties, as well a mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide, such as ethylene diamine ethylene oxides, ethylene diamine propylene oxides, mixtures thereof, and ethylene diamine EO-PO compounds, including those sold under the tradename Tetronic.

The composition used in the methods of the invention can also contain additional ingredients as necessary to assist in defoaming.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Methods of Application

In a further embodiment, a method for oxidizing or disinfecting a substrate is disclosed, wherein the method comprises contacting the substrate with an effective amount of the composition formed by combining the first part and the second part of the two-part oxidizing system of this invention. In this context, the substrate may be any surface or material in need of, or that would benefit from, such as food products such as meat, poultry, seafood, fruits, and vegetables, process or transport waters, hard surfaces, textiles, humans and animals.

Meat, Poultry, Seafood, Fruits, and Vegetables

Disinfecting compositions are applied to the surfaces of food products such as meat, poultry, seafood, fruits, and vegetables to reduce microorganisms such as spoilage and pathogenic microorganisms. The presence of microorganisms on a food product may cause everything from a consumer's perception of a lower quality product, to regulatory investigations and sanctions, to foodbourne illness and death. Examples of microorganisms include pathogenic microorganisms that can cause illness (e.g., *Listeria monocytogenes*, enterohemorrhagic *Escherichia coli*, *Salmonella* and the like) and spoilage organisms that can affect the taste, color, and/or smell of the final food product (e.g., *Pseudomonas, Acinetobacter, Moraxella, Alcaligenes, Flavobacterium, Erwinia*, and the like).

The compositions of the present invention may be applied to any food product that is consumed by a human or an animal. A food product includes both food and beverages, and specifically includes meat, poultry, seafood, fruits and vegetables. Some non-limiting examples of meat products include muscle meat or any portion thereof of any animal including beef, pork, veal, buffalo, or lamb. Some non-limiting examples of seafood include scallops, shrimp, crab, octopus, mussels, squid or lobsters. Some non-limiting examples of poultry include chicken, turkey, ostrich, game hen, squab, guinea foul, pheasant, duck, goose, and emu. Some non-limiting examples of fruits and vegetables include citrus fruits, tree fruits, tropical fruits, berries, lettuce, green beans, peas, carrots, tomatoes, mushrooms, potatoes, root vegetables, grains such as corn, wheat, oats, and animal feed, sprouts, seeds, and nuts.

When disinfecting meat, poultry, seafood, fruits and vegetables, the compositions of the invention may be applied to the surface of the food product in several ways including spraying, misting, rolling, and foaming the composition onto the food product and immersing the food product in the composition. The disinfecting composition may be applied in an injection such as in an injection solution, or the antimicrobial composition may be applied as part of a marinade or tenderizer that is applied to the food product. The application of the composition may be combined with physical agitation such as spraying with pressure, rubbing, brushing, etc. Application of the composition may be manual, or the composition may be applied in a spray booth. The disinfecting composition may be used on the food product once, and then discarded, or the disinfecting composition may be recycled.

When using a spray booth, the spray booth substantially confines the composition within the parameters of the booth. The production line moves the food product through the entryway of the spray booth into the spray heads where the food product is sprayed on all of its exterior surfaces with sprays within the booth. After a complete coverage of the composition and drainage of the composition, the food product exits the spray booth. The spray booth can comprise steam jets that can be used to apply the composition. These steam jets can be used in combination with cooling water to ensure that the treatment reaching the food product is less than 65° C., or less than 60° C. Lowering the temperature of the composition ensures than the food product is not altered or cooked by the temperature of the composition. The spray pattern can be virtually any useful spray pattern.

The spray can comprise of fog material that leaves a fogging apparatus as a dispersion of fog particles in a continuous atmosphere. Such a spray has no defined pattern. The spray can have a pattern such as a conical spray in which the angle between the perimeter of the spray ranges from less than a 180° to about 5°. Other spray patterns can also be useful. We have found that one preferred spray pattern involves a "fan" spray pattern in which the spray exits the spray head in a substantially planar form and the angle between the extent of the planar spray from edge to edge is about 20° or less, preferably about 15° or less. We found that such a spray is preferred due to the increased mechanical action and efficiency of disinfecting composition onto the carcass. When such a narrow angle fan spray is used in the spray cabinet enclosure to treat a food product, it has been found that the optimum distance between the spray head and the food product is less than about 100 centimeters, preferably about 20 to 80 centimeters, most preferably about 30 to 50 centimeters. Such a configuration efficiently transfers disinfecting composition to the food product for efficient reduction of microorganisms. Full cone spray nozzles will be advantageous in some applications.

There are a number of parameters which need to be considered if spraying is the application method of choice. The first parameter to determine is the pressure at which the composition is sprayed onto the food product. While spray pressures as low as about 25 psi (gauge) can be used with some valuable results, a higher spray pressure, greater than about 25, 50, 100, 150 psi and more preferably greater than about 200 psi are effective in reducing the populations of microorganisms due to the mechanical action of the spray on the food product surface and on the microorganism population remaining on the surface of the food product. The spray action is best at temperatures less than 65° C. If increased spray pressures are used, the disinfecting composition can be applied at lower temperatures, potentially resulting in substantial energy savings. Of course, there appears to be a relationship between application spray duration and antimicrobial efficacy. Most spray durations are as little as about 10 seconds can be used, it has been discovered that a preferred spray duration is from about 10 to about 30 seconds. Without wishing to be limited by theory, the increased antimicrobial efficacy resulting from the use of the higher spray pressure is believed to be due to an improvement in penetrating the surface of the food product, particularly an increased ability to reach into creases and crevices on the surface of the food product. Further, without wishing to be limited by theory, the increased antimicrobial efficacy resulting from the longer treatment time is believed to be due to an improvement in displacing "spent" solution from the surface of the food product (and therefore from the surface of adherent microorganisms) and replacing with fresh, full-strength AC compositions.

The food product may also be immersed into a container containing a quantity of disinfecting composition. The disinfecting composition is preferably agitated to increase the efficacy of this solution and the speed in which the solution kills microorganisms attached to the food product. Agitation can be obtained through conventional means including through ultrasonic means, aeration by bubbling air through the solution or by mechanical means, such as strainers, paddles, brushes or pump driven liquid jets. The disinfecting composition may also be heated to increase the efficacy of the solution in killing microorganisms.

In an embodiment of the present invention, the food product may be treated with a foaming version of the composition. The foam may be prepared by mixing foaming surfactants with the disinfecting composition at the time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfates, sulfonates, quaternary ammonium compounds, alkyl sarcosinates, betaines and alkyl amides. The foaming surfactant may be mixed at the time of use with the disinfecting composition. Use solution levels of foaming agents are from about 50 ppm to about 2.0 wt. %. At the time of use, compressed air may be injected into the mixture, which is then applied to the food product through a foam application device such as a tank foamer or an aspirated wall mounted foamer.

In an embodiment of the invention, the food product may be treated with a thickened or gelled version of the composition. In the thickened or gelled state, the disinfecting compositions remain in contact with the food product for longer periods of time, thus increasing the antimicrobial efficacy. The thickened or gel solution will also adhere to vertical surfaces. The disinfecting compositions may be thickened or gelled using existing technologies such as: xanthan gum, polymeric thickeners, cellulose thickeners, or the like. Rod micelle forming systems such as amine oxide and anionic counter ions could also be used. Typical use levels of thickeners or gel agents range from about 100 ppm to 10 wt. %.

In an embodiment of the invention, the food product may be treated with an electrostatically charged spray of the disinfecting composition. The disinfecting composition can be spray applied as charged droplets by using conventional electrostatic spray technologies including inductively charged methodologies. As charged droplets, the disinfecting composition will be attracted to opposite or differentially charged surfaces such as the surface of a food product. As a result, more disinfecting composition will be applied to the food product surface and less composition will miss the intended target, commonly called overspray. The charged droplets will also provide an evenly distributed composition layer on the food product surface. The charged droplets size will range from about 10 microns to about 500 microns.

In another embodiment of the invention, the food product may be subjected to a vacuum treatment either before applying the disinfecting composition, during the application of the disinfecting composition, or after applying the disinfecting composition. When the food product is subjected to a vacuum treatment in conjunction with application of the disinfecting composition, the penetration of the disinfecting composition into the food product substructure is enhanced. As a result, antimicrobial efficacy is improved. The amount of vacuum utilized is from about 2 inches of mercury to about 29 inches of mercury. This embodiment is particularly effective when using it on carcasses such as meat and poultry carcasses.

In another embodiment of the invention, the food product may be subjected to an activating light source following application of the disinfecting composition. The activating light can improve the antimicrobial efficacy of the disinfecting composition. The light source can be ultraviolet, infrared, from the visible spectrum, or a combination thereof.

The disinfecting composition can optionally be combined with a thermal intervention process which occurs either before, during, or after the application of the disinfecting composition. The thermal intervention process may employ hot water or dry heat. In the case of a hot water thermal process the food product is enclosed in a chamber at atmospheric pressure. The chamber is filled with condensing steam (finally divided liquid water) fresh short duration, quickly vented, then cooled to prevent browning or discoloring of the food product. The duration of the steam thermal process may be from about 5 seconds to about 30 seconds. The chamber temperature may reach from about 50° C. to about 98° C. Similarly with dry heat, the food product is placed in a chamber into which heated air is directed. The air is heated from about 65° C. to about 260° C. The food product is allowed from about 5 to about 30 seconds contact time with the heated air, the chamber is vented, and the food product is cooled.

When applying the disinfecting composition to a food product such as meat, poultry, seafood, fruits, and vegetables, it may be desirable to formulate the disinfecting composition with additional functional ingredients such as wetting agents, hydrotropes, thickeners, surfactants, foaming agent, pigments, dyes and the like. Examples of additional functional ingredients that may be added are described under the additional functional ingredient section herein. Further, when applying the disinfecting compositions of the invention to a food product, it may be beneficial to formulate the disinfecting composition using GRAS (general recognized as safe) or food additive ingredients that may be applied directly to the food product, and do not need to be rinsed off of the food product.

The compositions preferably produce at least a one $\log_{10}$ reduction in microorganism population, and preferably at least a two $\log_{10}$ reduction or a three $\log_{10}$ reduction.

It has been found that the volume of solution per pound of food stuff is an important parameter in the antimicrobial efficacy of AC compositions. Preferred volumes for treated poultry, fish, fruits and vegetables and red meat pieces/trim are from 0.5 oz/lb to 3.0 oz/lb, and more preferably, 1.0-2.0 oz/lb of food stuff in dip and spray applications. For beef carcasses, the preferred volumes range from 0.5 to 2.5 gallons per side of beef, and more preferably from 1.0-2.0 gallon/side.

Treatment of food products with a disinfecting composition is described in greater detail in U.S. Pat. Nos. 5,389,390, 5,409,713, 6,063,425, 6,183,807, 6,113,963, 6,514,556, and 6,545,047, the disclosures of which are incorporated by reference herein in their entirety.

Process or Transport Waters

In addition to applying the disinfecting composition to a food product, the disinfecting composition may be added to water used to transport and/or store food product such as fruits, vegetables, grains, sprouts, seeds and nuts. For example, in specific applications, food products may be transported through water streams by food handling equipment used at the processing plant. After picking, fruits, and vegetables, sprouts, seeds, and nuts are introduced into a flume system wherein water acts as a transport medium and a cleaning medium. Water may be used to support and transport the food products from an unloading site to a final storage or packing or processing location. During the transport, water can take a food item from an initial location through a series of somewhat separate stages to a final station where the food product is removed from the water and packed. The water within each stage may have a varying degree of organic load in the form of any number of sediments and soluble materials. This water may be recycled.

Water can also be used in some of the processes and stages to further, clean, cool, cook, or otherwise modify a food in some fashion prior to packaging. Process water as defined above may sometimes be used once and discarded. However, often times a major portion of this processed water is reused and is therefore subject to organic and microbial contamination. In some stages of processed water stream is also used to transport the food. In other stages, the processed water may be a separate stream and is recycled apart from the transport water. In either situation, the processed water becomes contaminated with organic matter from the food, providing new transformed microbial growth in the water. Examples of different types of processed waters are vegetables washers, vegetables cooling basket, poultry chillers, and meat washers.

Given the nature of the food as well as the presence of sediments and soluble materials, the water, flume, and other transport or processing equipment may be subject to the growth of unwanted microorganisms. These microorganisms are generally undesirable to the food, the water, the flume and may cause buildup on all water contact surfaces of slime or biofilm which requires frequent cleaning to remove. Further, because the transport water, processed water, and equipment are in contact with food products, the control of unwanted microorganisms presents certain problems created by a food contact environment containing microorganisms.

In the preceding discussion, it has been assumed that the transport or processed water has contacted the food prior to packaging. There is also a stream used to process certain types of food subsequent to packaging. Some foods are often times heated, cooled, or otherwise processed after being placed into packages made of metal, glass, or plastic containers, for example, bottled beer, pasteurizers, can cookers, or can coolers. In all cases, contamination of the aqueous streams by food occurs due to leakage from defective packages or spillage on the outside of the package during the packaging operation. These packaged food process streams also are therefore subject to unwanted microbial growth and high concentrations of organic matter similar to prepackage process and transport water.

The disinfecting compositions of the present invention may be used to reduce the presence of microorganisms in the water that is used to transport, clean, cool, heat, cook or otherwise modify a food product. In addition, the disinfecting compositions may be used in flume waters, cooling tower water, livestock drinking water, and equipment and facility cleaning solutions. The use of disinfecting compositions in transport waters or process streams is described in greater details in U.S. Pat. Nos. 5,409,713, and 5,674,583, the disclosures of which are incorporated by reference herein, in their entirety.

The compositions may include additional functional ingredients such as those described herein. When applying disinfecting compositions to process waters or transport streams, it may be preferable to use GRAS or food additive ingredients.

The compositions preferably produce at least a one $\log_{10}$ reduction in the microorganism population, and preferably at least a two $\log_{10}$ reduction or a three $\log_{10}$ reduction.

Hard Surfaces and Textiles

The present oxidizing and disinfecting compositions may be used to disinfect, oxidize; and/or bleach hard surfaces and textiles used in processing facilities such as dairy, brewing, and food processing facilities, healthcare facilities such as hospitals, clinics, surgical centers, dental offices, and laboratories, long-term care facilities such as nursing homes, farms, and consumer homes.

The oxidizing and disinfecting compositions may be used to disinfect environmental surfaces such as floors, walls, ceilings, and drains. The compositions may be used to disinfect equipment such as food processing equipment, dairy processing equipment, brewery equipment, and the like. The compositions may be used to disinfect tools and instruments such as medical tools and instruments, dental tools and instruments, as well as equipment used in the healthcare industries and institutional kitchens, knives, wares such as pots, pans, and dishes, cutting equipment, and the like. The compositions may to disinfect a variety of surfaces including food contact surfaces in food, dairy, and brewing facilities, countertops, furniture, sinks, and the like. Finally, the compositions may be used to disinfect, and bleach textiles such as clothing, protective clothing, laboratory clothing, surgical clothing, patient clothing, carpet, bedding, towels, linens, and the like.

The composition may be employed by dipping a surface into the composition, soaking a surface in the composition, spraying, wiping, foaming, misting, rolling, and fogging the composition onto a surface. The composition may be applied manually or using equipment such as a spray bottle or machine such as a spray machine, foam machine, and the like. The composition can also be used inside a machine such as a warewashing machine or laundry machine. The composition may be applied at a variety of temperatures including ambient temperature or at use temperatures in the range from about 4° C. to about 65° C.

The compositions may include additional functional ingredients such as those described herein. When applying oxidizing and disinfecting compositions to hard surfaces or textiles, the compositions preferably produce at least one $\log_{10}$ reduction in the microorganism population of the hard surface or textile, and preferably at least a two $\log_{10}$ reduction or a three $\log_{10}$ reduction.

Methods of disinfecting hard surfaces are described in greater detail in U.S. Pat. Nos. 5,200,189, 5,314,687, and 5,718,910, the disclosures of which are incorporated by reference herein in their entirety.

Humans and Animals

The compositions of the invention may be applied to humans and animals, for example as antimicrobial skincare compositions, teat dips, or hoof treatment.

Proper skincare in humans has long been cited as an effective way of reducing the spread of germs, diseases, and other contaminates. Proper skincare is especially important in industries where bacteria and microorganisms are particularly problematic such as the healthcare industries, patient care industries, and the food and beverage industries. Accordingly, the present invention may be formulated to be used as an antimicrobial handsoap, antimicrobial hand lotion, antimicrobial hand sanitizer, surgical scrub, healthcare personnel handwash, and antiseptic for injection sites, or patient preoperative site preparation. When formulating the present compositions for use as a skincare composition, it may be desirable to incorporate other ingredients that increase the effectiveness of the composition or add some additional benefits such as skin conditioners, emulsifiers, thickeners, and the like.

The present composition may also be formulated to be applied to an animal, for example, as a teat dip. Commercial teat dips are known as a method of reducing bovine mastitis in dairy herds. Mastitis is one of the most common and economically costly diseases confronting milk producers. Economic losses result from poor milk quality, lower milk production, and potential culling of chronically infected animals. The use of disinfectant solutions both before and after milking has found great success in preventing mastitis, particularly disinfectants based on AC compositions such as those described in U.S. Pat. Nos. 6,524,624, and 6,699,510, the disclosures of which are incorporated by reference herein, in their entirety. When formulating the present compositions for a teat dip, it may be desirable to add additional ingredients that enhance the effectiveness of the composition or provide additional benefit such as color to act as an indicator to a farmer that the disinfectant has been properly applied, and a rheology modifier or a thickener to allow the teat dip composition to cling to the teat of the animal.

Finally, the composition may be formulated to be used as a foot bath or hoof treatment for farms to prevent the spread of diseases. For example, the composition may be formulated so that farm works walk through the composition and thereby prevent any microorganisms on their boots from spreading. Alternatively, the composition may be formulated in such a way that animals walk through the composition, thereby preventing the spread of microorganisms, and also providing an opportunity to treat any infections on the hooves of the animals. When the composition is formulated as a foot bath or hoof treatment, it may be formulated in a variety of physical forms including as a water thin liquid and as a foam.

Methods of Mixing

In a further aspect of this invention, the invention is directed to a method for making a composition comprising combining the first part and the second part of the two-part oxidizing/disinfecting system. In one embodiment, the first and second parts are both aqueous solutions, emulsions, microemulsions, creams or gels, and may be adapted to be combined in equal or different volumes. In another embodiment, at least one of the first or second parts is in a concentrated, non-aqueous or solid form, and the concentrated, non-aqueous or solid form is first diluted with or dissolved in water, and then combined with the other part. Alternatively, the dilution or dissolving step can occur prior to combination with the other part, or simultaneous with combination.

The compositions may be combined in one container and then subsequently dispensed. Alternatively, the compositions may be dispensed separately and combined on the desired surface. For example, the individual components of the two-part oxidizing system may be located in separate chambers of a two-part spray bottle where the individual components are mixed on the surface after being sprayed. The individual components may be combined inside a piece of equipment such as a spray cabinet for food products, a laundry machine, or a warewashing machine.

The following examples are provided for the purpose of illustration, not limitation.

EXAMPLES

Wastewater Treatment Test Method

The wastewater test method was used to test the impact of a citric acid based acidified sodium chlorite formula versus a sodium acid sulfate based acidified sodium chlorite formula on various wastewater characteristics. Acidified sodium chlorite use solutions were prepared using citric acid and sodium acid sulfate. The citric acid formula and sodium acid sulfate formula were prepared, mixed and diluted as shown in Table 2.

TABLE 2

Citric Acid and Sodium Acid Sulfate Formulas

| Citric Acid Formula | | Sodium Acid Sulfate Formula | |
|---|---|---|---|
| Stock Solution | Use Solution | Stock Solution | Use Solution |
| 25% Sodium Chlorite | 1000 ppm Sodium Chlorite | 25% Sodium Chlorite | 1000 ppm Sodium Chlorite |
| 50% Citric Acid | 6000 ppm Citric Acid | 10% Sodium Acid Sulfate | 1000 ppm Sodium Acid Sulfate |
| pH = 2.5 to 2.7 (target 2.5) | 1000 ppm Acidified Sodium Chlorite | pH = 2.5 to 2.7 (target 2.5) | 1000 ppm Acidified Sodium Chlorite |

This test used the Jar Test Profile (ASTM Designation: D 2035-80 Standard Practice for Coagulation-Flocculation Jar Test of Water), which is incorporated by reference herein in its entirety. For this test, wastewater was pulled out of the wastewater stream of a chicken processing plant.

Antimicrobial Efficacy Test

The antimicrobial efficacy test was used to compare the efficacy of the citric acid formula and the sodium acid sulfate formula of Table 2 against *Escherichia coli, Salmonella*, and *Campylobacter*. For this test, the acidified sodium chlorite solutions were placed in the post-chill dip tank of a chicken processing plant at a concentration of 1000 ppm sodium chlorite. The temperature of the dip tank was the temperature of the water coming into the plant (approximately 50 to 70° F.). The test was run at a chicken processing plant. During the test, chicken carcasses were brought out of the chiller and into the dip tank. The carcasses were placed in the dip tank for approximately 15 seconds. Carcasses were picked at random and subjected to the USDA Bird Rinse Protocol, which is incorporated by reference herein in its entirety, in order to determine the antimicrobial efficacy of the acidified sodium chlorite solution. For the control, the birds were pulled off the line after the chiller but before the dip tank and also subjected to the USDA Bird Rinse Protocol. For both the experimental and control tests, the number of incidence counts were recorded, meaning that if bacteria were found on a carcass, one incidence count was recorded.

Example 1

Impact of Ferric Sulfate Addition on COD

As previously discussed, coagulants are often used in wastewater treatment to remove charges from particles in solution and make them more likely to form larger particles that can float to the top and be skimmed off and removed. However, when acidified sodium chlorite solutions are present in the wastewater, the type of acid used to make the acidified sodium chlorite solution can impact the wastewater treatment process. Example 1 tested the impact of a known coagulant, ferric sulfate, on the COD (chemical oxygen demand) when the acidified sodium chlorite solutions of Table 2 are present. For this example, the wastewater treatment test method was used. After wastewater samples were pulled, various levels of ferric sulfate were added to the samples. The samples were then subjected to the Jar Test Profile and the mg/L COD was recorded.

Figure 2:
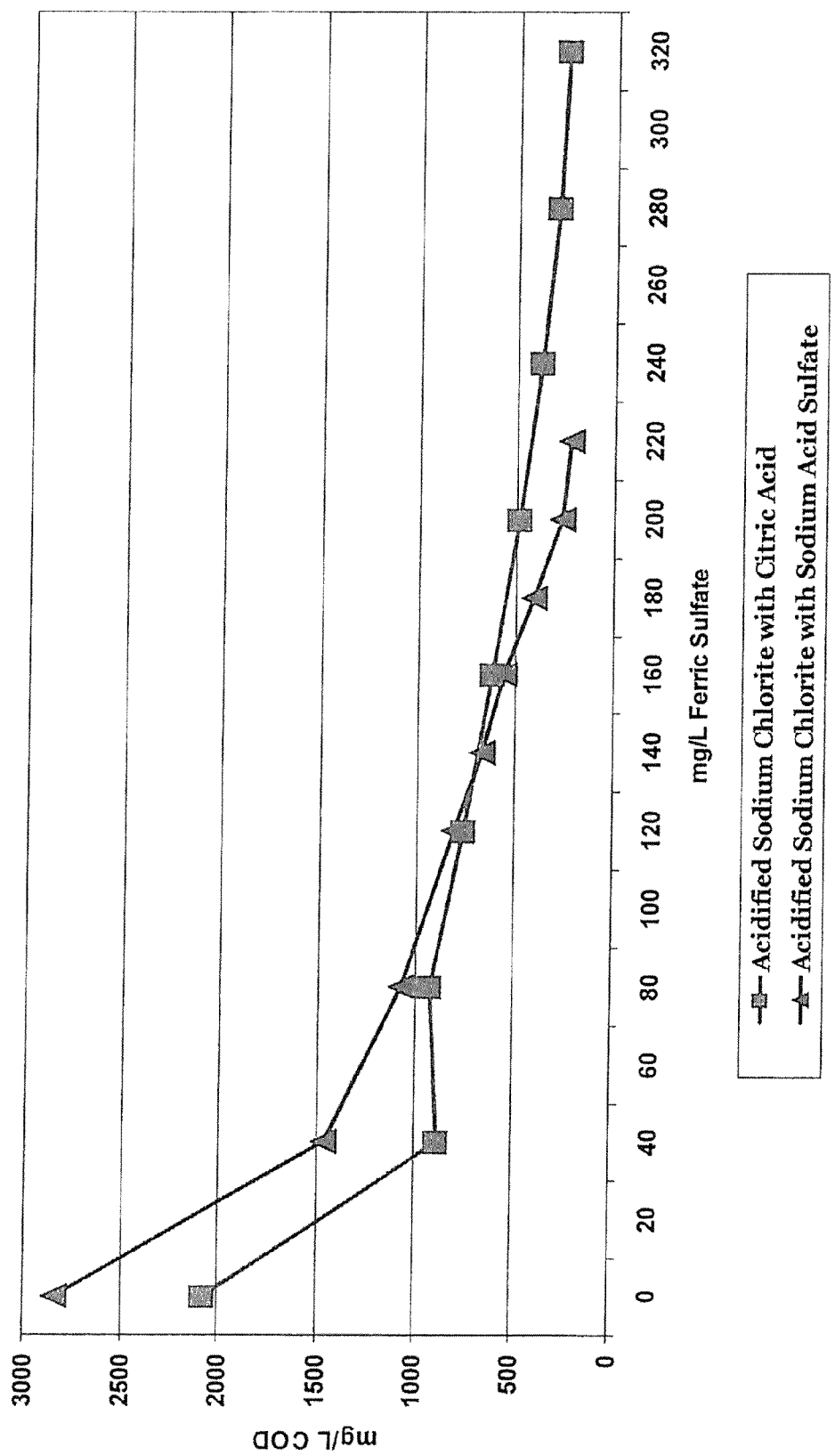

FIGS. 1 and 2 show the impact of acidified sodium chlorite compositions made with citric acid and sodium acid sulfate on the COD. The COD is a measure of the level of organics in the water. Organics are undesirable because they contribute to bacteria growth in the water. A high COD means that there is a high organic level in the water and those organics must be removed. Therefore, the lower the COD, the less the wastewater needs to be treated to remove the organics. In FIGS. 1 and 2, as the ferric sulfate concentration increases, the COD level decreases for both the citric acid formula and the sodium acid sulfate formula. Initially, the sodium acid sulfate formula has a higher COD than the citric acid formula, however, after the concentration of ferric sulfate reaches 140 mg/L, the sodium acid sulfate formula begins to have a lower COD than the citric acid formula. Because the goal in wastewater treatment is to have the lowest COD possible, sodium acid sulfate is preferred over citric acid because as the concentration of the coagulant ferric sulfate increases, it is clear that sodium acid sulfate has the lower COD level of the two acids.

Example 2

Impact of Ferric Sulfate Addition of Phosphorous Removal

Again, ferric sulfate is a known coagulant used in wastewater treatment that can react with acidified sodium chlorite solutions in the waste water. As previously discussed, phosphorous is one of many species present in the wastewater that must be removed. Example 2 tested the impact of ferric sulfate concentration on phosphorous level left in the wastewater when the acidified sodium chlorite solutions of Table 2 are present. For this example, the wastewater treatment test method was used. After wastewater samples were pulled, various levels of ferric sulfate were added to the samples. The samples were then subjected to the Jar Test Profile and the mg/L phosphorous was recorded.

Figure 3:
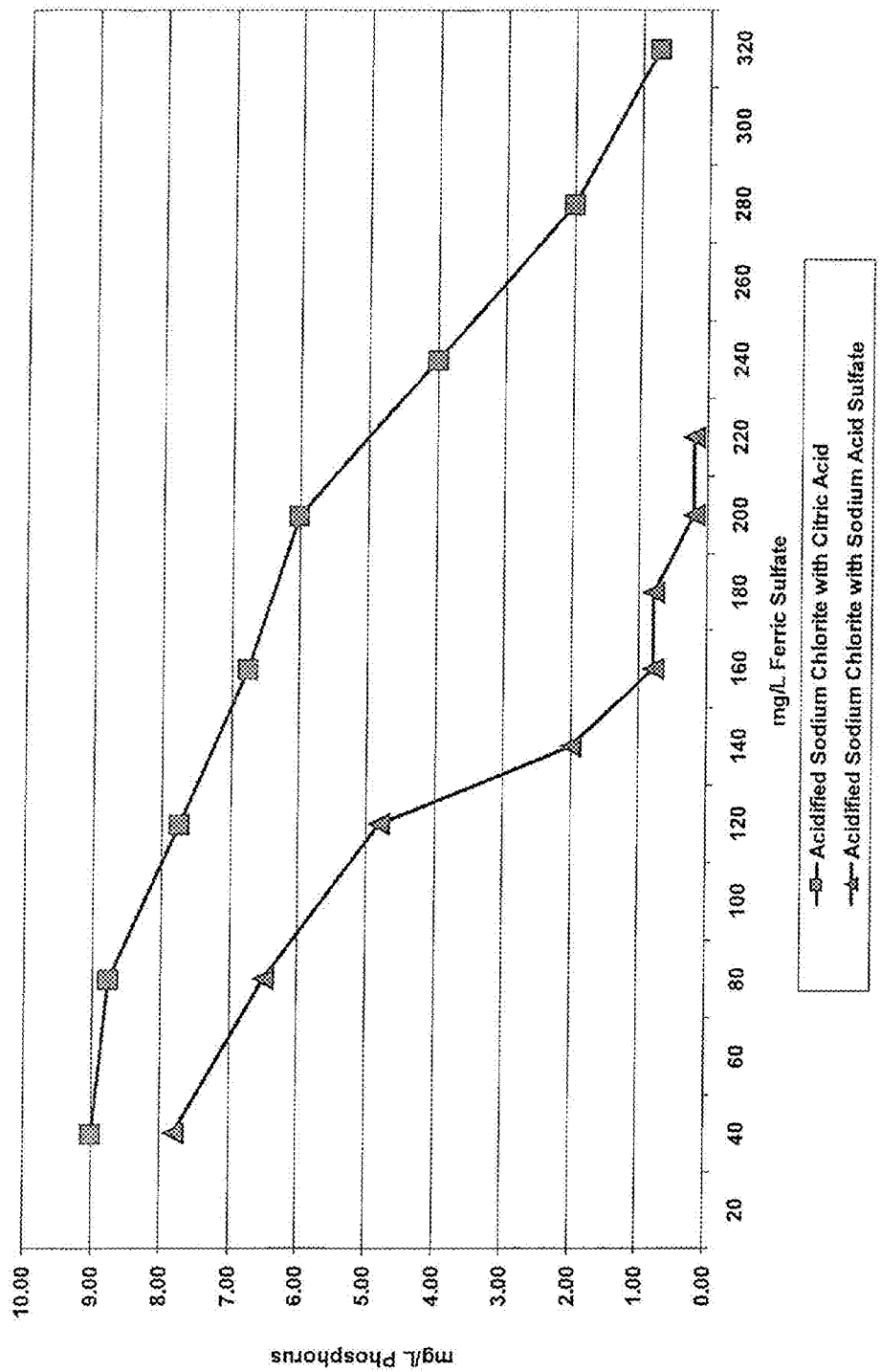
FIG. 3 is a graphical depiction of the impact of acidified sodium chlorite compositions made with citric acid and sodium acid sulfate on the phosphorous level in wastewater.

FIG. 3 shows the impact of acidified sodium chlorite compositions made with citric acid and sodium acid sulfate on the phosphorous level in the wastewater. The sodium acid sulfate formula always has a lower level of phosphorous in the wastewater. However, when the ferric sulfate concentration reaches 140 mg/L, the level of phosphorous in the wastewater drops significantly for the sodium acid sulfate formula. Once the ferric sulfate concentration reaches 200 mg/L, the level of phosphorous in the wastewater with the sodium acid sulfate formula is almost zero, while the level of phosphorous in the water for the citric acid formula is still at 6.00. The low level of phosphorous in the wastewater of the sodium acid sulfate formula makes that formula much more desirable over the citric acid formula because the plant will be able to remove the phosphorous more readily and will not have to pay to dispose of the phosphorous or have fines imposed for releasing the phosphorous into the environment.

Example 3

Impact of Ferric Sulfate on Turbidity

As previously discussed, high turbidity or a high solid concentration in wastewater is undesirable for several reasons. High turbidity creates places for bacteria to grow. High turbidity also increases COD which is undesirable for the reasons previously discussed in Example 1. Finally, high turbidity or high solid is aesthetically undesirable, particularly in drinking water. Example 3 tested the impact of ferric sulfate concentration on turbidity in the wastewater when the acidified sodium chlorite solutions of Table 2 are present. For this example, the wastewater treatment test method was used. After wastewater samples were pulled, various levels of ferric sulfate were added to the samples. The samples were then subjected to the Jar Test Profile and the turbidity was recorded.

Figure 4:
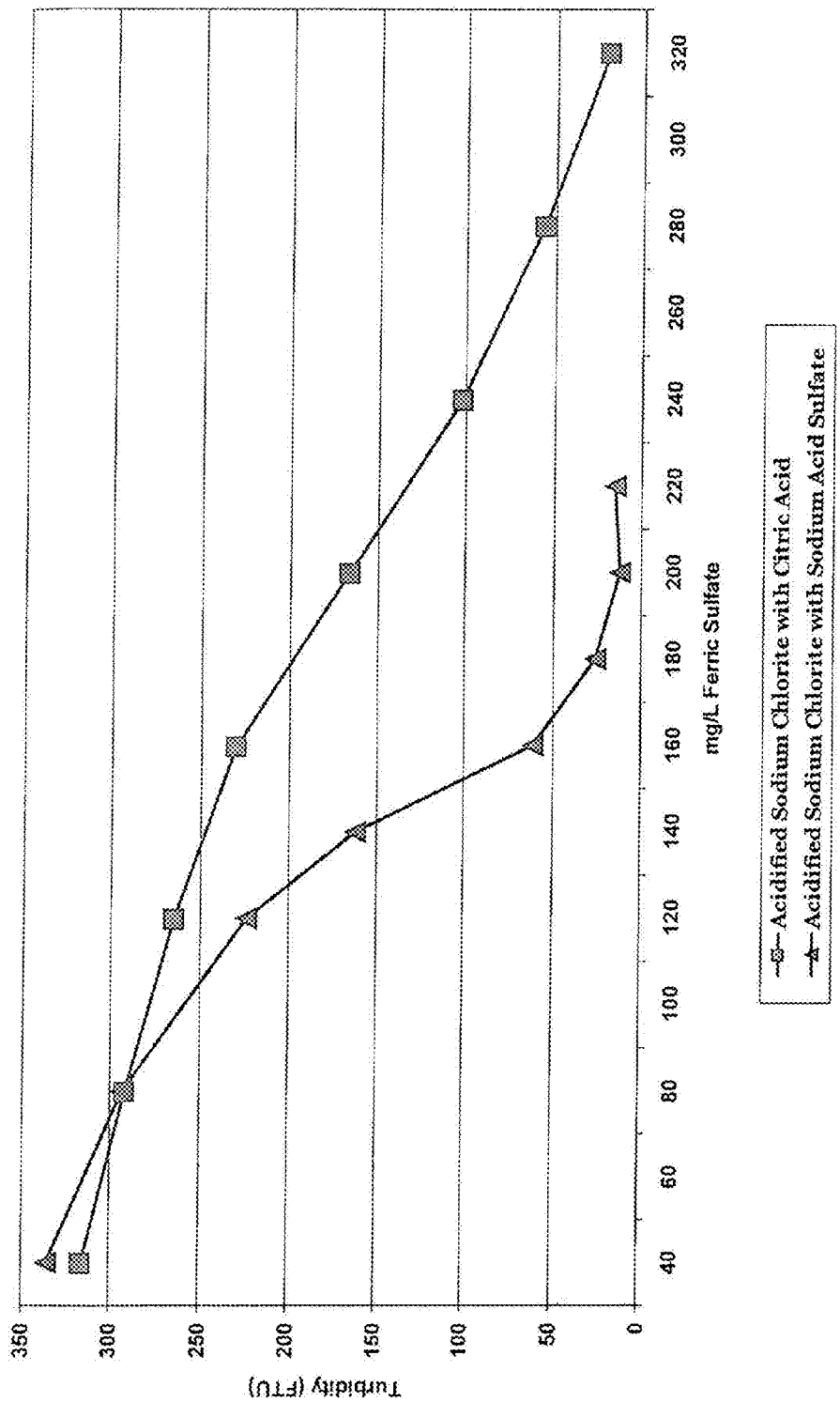
FIG. 4 is a graphical depiction of the impact of acidified sodium chlorite compositions made with citric acid and sodium acid sulfate on the turbidity of wastewater.

FIG. 4 shows the impact of acidified sodium chlorite compositions made with citric acid and sodium acid sulfate on the turbidity of the wastewater. Initially, the sodium acid sulfate formula starts out having a higher turbidity than the citric acid formula. However, the sodium acid sulfate solution quickly drops below the citric acid solution in terms of turbidity. As the ferric sulfate concentration reaches 160 mg/L, the sodium acid sulfate solution has 50 FTU compared to approximately 225 FTU with the citric acid formula. As the ferric sulfate concentration approaches 200 mg/L, the turbidity of the sodium acid sulfate formula approaches 0 while the turbidity of the citric acid formula remains about 150.

Example 4

Impact of Ferric Sulfate on pH

In order for wastewater to be released into the environment, the wastewater has to have a pH typically in the range of 5 to 9. If the pH is too low, chemicals needed to be added to increase the pH between 5 and 9, which increases the costs of wastewater treatment. Example 4 tested the impact of ferric sulfate concentration on pH when the acidified sodium chlorite solutions of Table 2 are present. For this example, the wastewater treatment test method was used. After wastewater samples were pulled, various levels of ferric sulfate were added to the samples. The samples were then subjected to the Jar Test Profile and the pH was measured and recorded.

Figure 5:
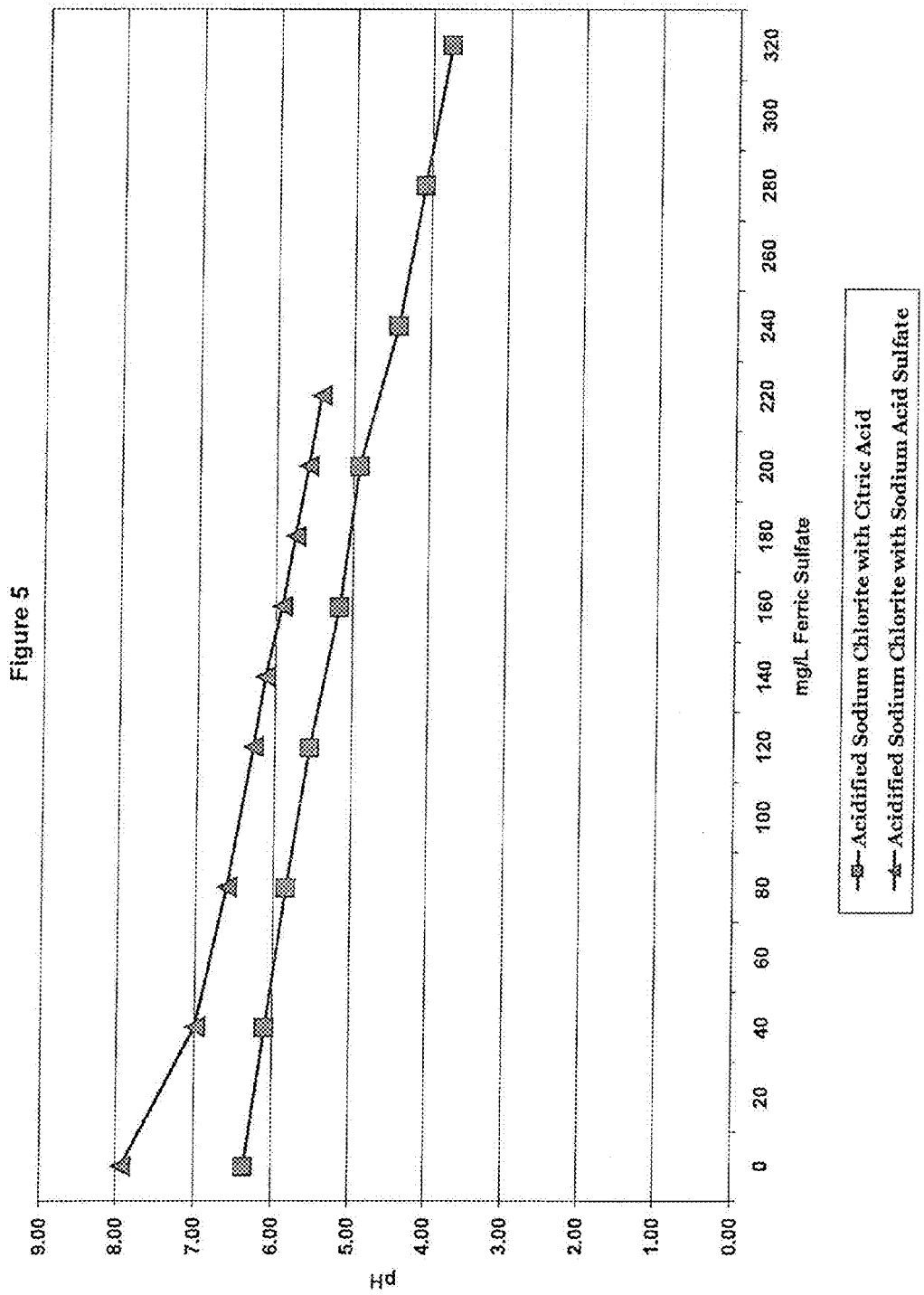
FIG. 5 is a graphical depiction of the impact of acidified sodium chlorite compositions made with citric acid and sodium acid sulfate on the pH of wastewater.

FIG. 5 shows the impact of acidified sodium chlorite compositions made with citric acid and sodium acid sulfate on a pH of the wastewater. Generally speaking the pH of the sodium acid sulfate based solution always remains between 5 and 8, whereas the pH of the citric acid based solution drops below 5 as the concentration of ferric sulfate approaches 200 mg/L. Once the pH of the citric acid solution drops below 5, chemicals will need to be added to increase the pH above 5 before the wastewater can be discharged into the environment which increases the cost of wastewater treatment. Therefore, the sodium sulfate solution is more desirable because the pH always remains above 5 and additional chemicals will not need to be added.

Example 5

Antimicrobial Efficacy Against Escherichia coli

Example 5 tested the antimicrobial efficacy of the acidified sodium chlorite solutions of Table 2 against *Escherichia coli*. For this example, the antimicrobial efficacy test was used and the number of incidence counts were recorded. The acidified sodium chlorite solutions were tested against large chicken carcasses and small chicken carcasses. Forty chicken carcasses were tested for each control and experimental.

Figure 6:
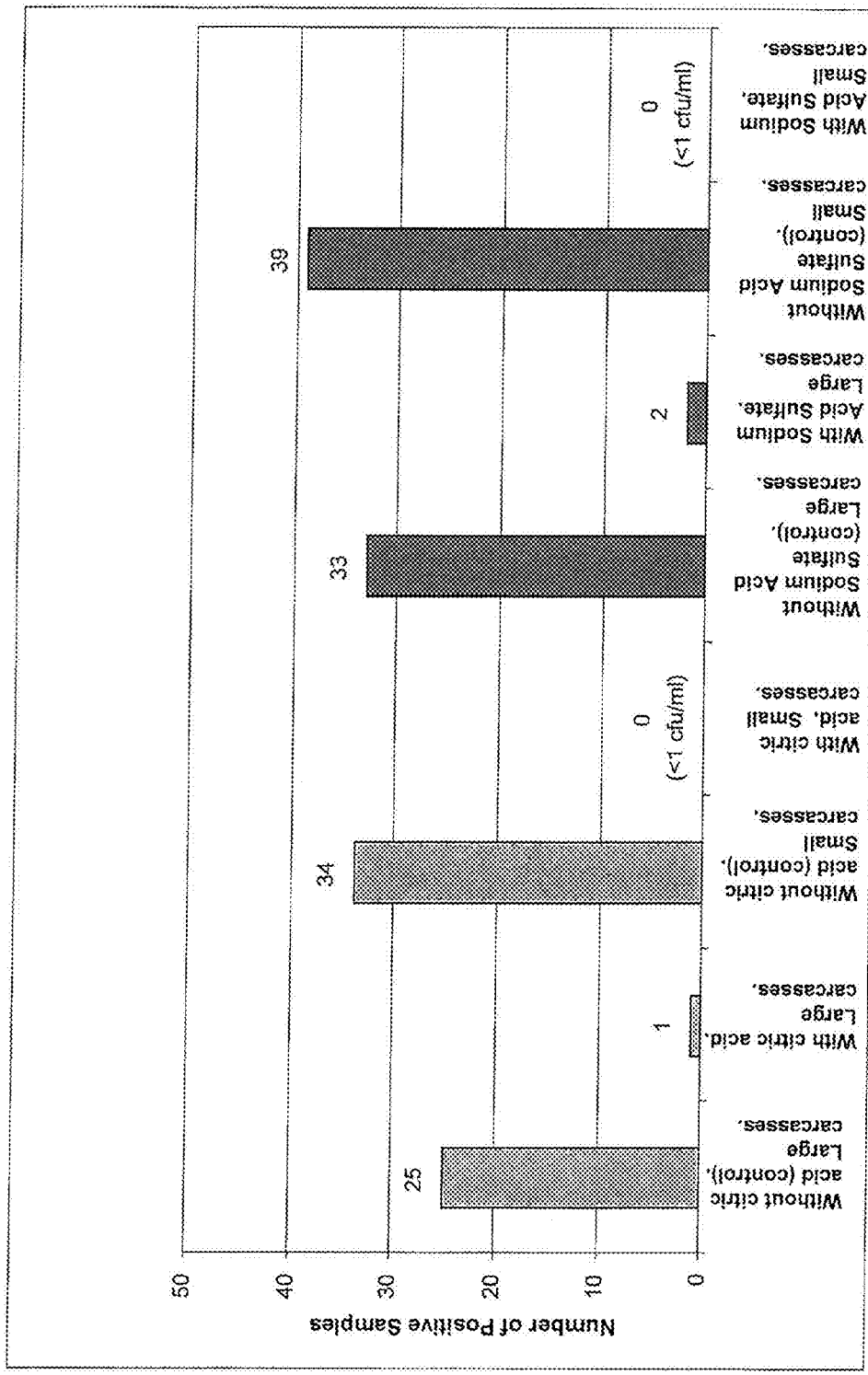
FIG. 6 is a graphical depiction of the antimicrobial efficacy of acidified sodium chlorite compositions made with citric acid and sodium acid sulfate against *Escherichia coli* on large and small chicken carcasses.

FIG. 6 shows the antimicrobial efficacy of acidified sodium chlorite compositions made with citric acid and sodium acid sulfate against *Escherichia coli* on large and small chicken carcasses. FIG. 6 shows that the sodium acid sulfate formula has comparable antimicrobial efficacy to the citric acid based formula. Both the citric acid based formula and the sodium acid based formula when tested on small chicken carcasses have zero incidence counts. The antimicrobial efficacy test used has a lower limit of detection of less than 1 cfu/mL.

Example 6

Antimicrobial Efficacy Against Salmonella

Figure 7:
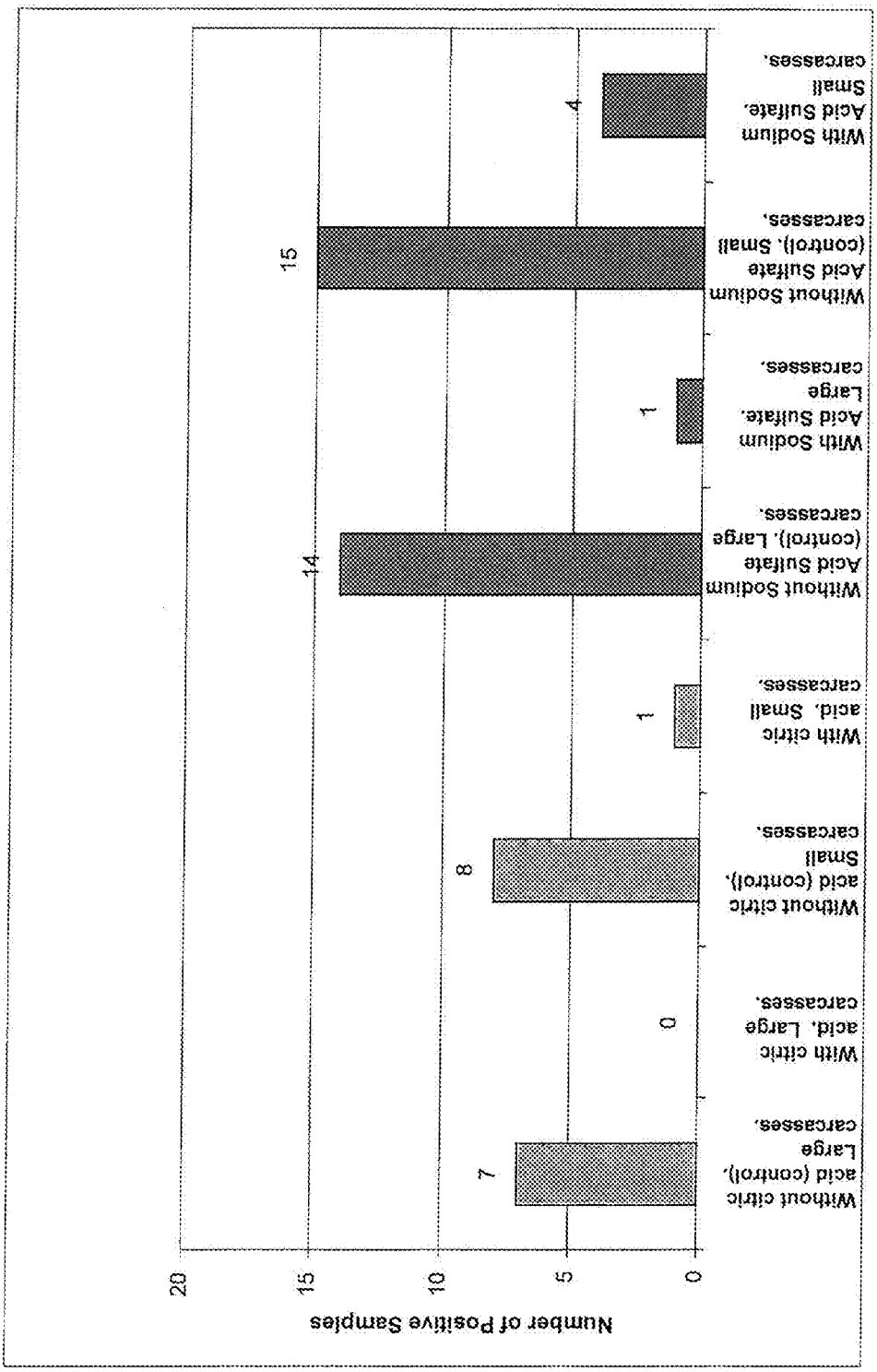
FIG. 7 is a graphical depiction of the antimicrobial efficacy of acidified sodium chlorite compositions made with citric acid and sodium acid sulfate against *Salmonella* on large and small chicken carcasses.

Example 6 tested the antimicrobial efficacy of the acidified sodium chlorite solutions of Table 2 against *Salmonella*. For this example, the antimicrobial efficacy test was used and the number of incidence counts were recorded. The acidified sodium chlorite solutions were tested against large chicken carcasses and small chicken carcasses. Forty chicken carcasses were tested for each control and experimental. FIG. 7 shows the antimicrobial efficacy of acidified sodium chlorite compositions made with citric acid and sodium acid sulfate against *Salmonella* on large and small chicken carcasses. FIG. 7 shows that the sodium acid sulfate formula have comparable antimicrobial efficacy to the citric acid based formula. While the number of incidence counts for chicken carcasses treated with sodium acid sulfate formula is higher than those chicken carcasses treated with acidic acid based formula, the number of incidence counts for the sodium acid sulfate control were significantly higher than the number of incidence counts for the citric acid control.

Example 7

Antimicrobial Efficacy Against Campylobacter

Example 7 tested the antimicrobial efficacy of the acidified sodium chlorite solutions of Table 2 against *Campylobacter*. For this example, the antimicrobial efficacy test was used and the number of incidence counts were recorded. The acidified sodium chlorite solutions were tested against large chicken carcasses and small chicken carcasses. Forty chicken carcasses were tested for each control and experimental.

Figure 8:
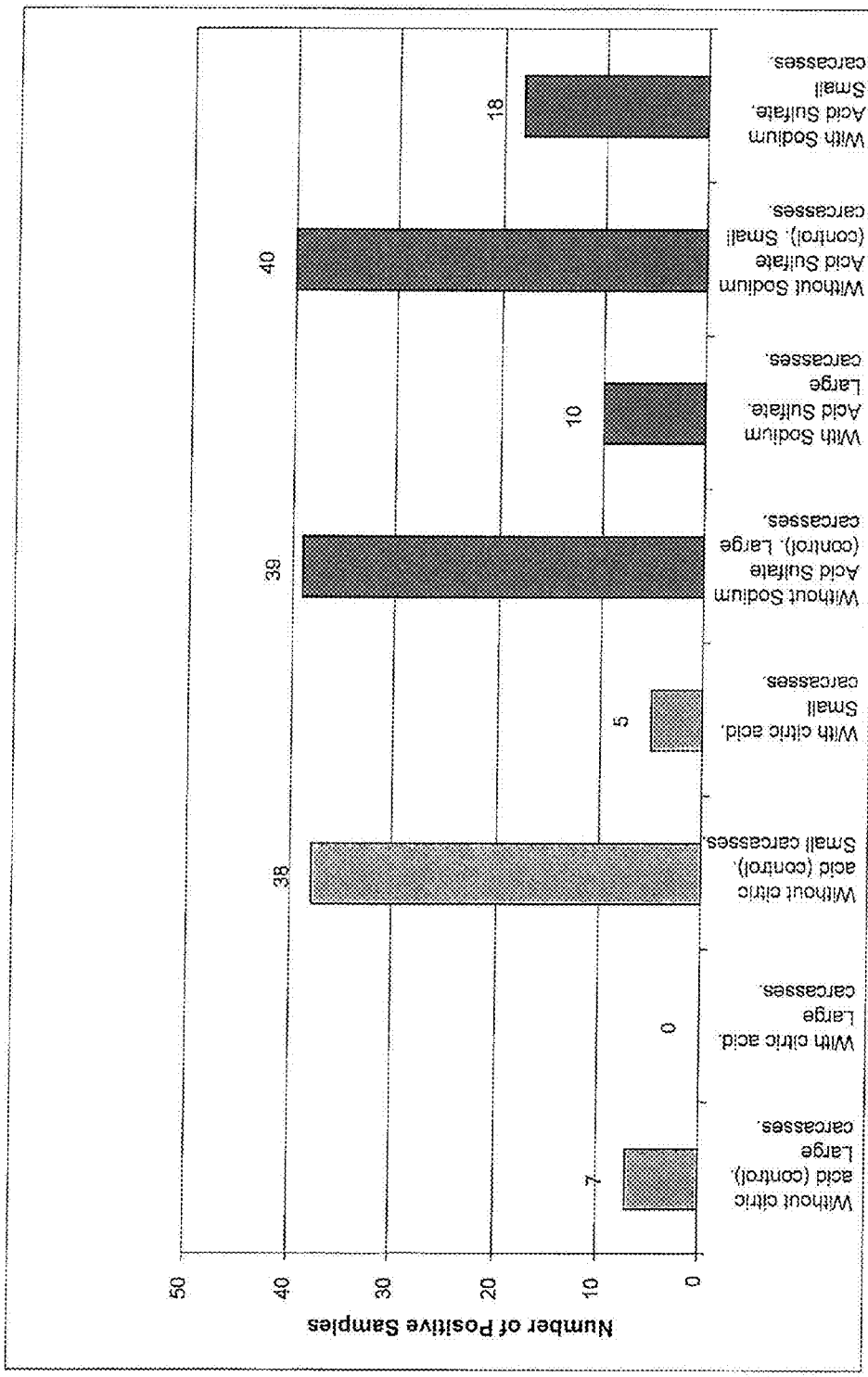
FIG. 8 is a graphical depiction of the antimicrobial efficacy of acidified sodium chlorite compositions made with citric acid compared to acidified sodium chlorite compositions made with sodium acid sulfate against *Campylobacter* on large and small chicken carcasses.

FIG. 8 shows the antimicrobial efficacy of acidified sodium chlorite compositions made with citric acid was only slightly better than the antimicrobial efficacy of acidified sodium chlorite compositions made with sodium acid sulfate against *Campylobacter* on large and small chicken carcasses. The acidified sodium chlorite compositions made with sodium acid sulfate were still very effective at reducing the number of incidence counts on large and small chicken carcasses.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A two-part oxidizing system consisting of a first part and a second part adapted to be mixed to yield an aqueous oxidizing composition, wherein the first part consists of a chlorite and an optional additional ingredient, and the second part consists of a sodium acid sulfate or a chemical moiety that provides the bisulfate ion in situ, and an optional additional ingredient, wherein the additional ingredient in either the first part, the second part or both the first and second parts is selected from the group consisting of chelating agents, additional acids, hydrotropes, thickening or gelling agents, additional antimicrobial agents, carriers, wetting or defoaming agents, foaming agents, builders, textual modifiers, film-forming agents, rheology modifiers, surfactants, flavoring aids, colorants, fragrances, skin conditioning agents, and mixtures thereof, and wherein the first part and the second part when mixed form about 10 ppm to about 10,000 pm chlorous acid.

2. The system of claim 1, wherein the chemical moiety is selected from the group consisting of potassium hydrogen sulfate, cesium hydrogen sulfate, and buffered sulfuric acid.

3. The system of claim 1, wherein the chlorite is a metal chlorite.

4. The system of claim 3, wherein the metal chlorite is an alkali or alkaline earth metal chlorite.

5. The system of claim 4, wherein the metal chlorite is sodium chlorite or potassium chlorite.

6. The system of claim 1, wherein the chlorite is present in the first part in an amount so that when combined with the second part it is present within the oxidizing composition at a concentration ranging from about 0.001% to about 2.0% by weight.

7. The system of claim 1, wherein the acid is present in the second part in an amount so that when combined with the first part it is present within the oxidizing composition at a concentration ranging from about 0.001% to about 2.0% by weight.

8. The system of claim 1, wherein the acid is present in the second part in an amount so that when combined with the first part the pH of the oxidizing composition is from about 1 to about 4.

9. The system of claim 1, wherein both the first part and the second part are independently in the form of an aqueous solution, emulsion, microemulsion, cream, gel, solid block, tablet, powder, pellet, or prill.

10. A two-part disinfecting system consisting of a first part and a second part adapting to be mixed to yield an aqueous disinfecting composition, wherein the first part consists of a chlorite and an optional additional ingredient, and the second part consists of sodium acid sulfate or a chemical moiety that provides the bisulfate ion in situ, and an optional additional ingredient wherein the additional ingredient in either the first part, the second part or both the first and second parts is selected from the group consisting of chelating agents, additional acids, hydrotropes, thickening or gelling agents, additional antimicrobial agents, carriers, wetting or defoaming agents, foaming agents, builders, textual modifiers, film-forming agents, rheology modifiers, surfactants, flavoring aids, colorants, fragrances, skin conditioning agents, and mixtures thereof, and wherein the first part and the second part when mixed form about 10 ppm to about 10,000 pm chlorous acid.

11. The system of claim 10, wherein the chemical moiety is selected from the group consisting of potassium hydrogen sulfate, cesium hydrogen sulfate, and buffered sulfuric acid.

12. The system of claim 10, wherein the chlorite is a metal chlorite.

13. The system of claim 12, wherein the metal chlorite is an alkali or alkaline earth metal chlorite.

14. The system of claim 13, wherein the metal chlorite is sodium chlorite or potassium chlorite.

15. The system of claim 10, wherein the chlorite is present in the first part in an amount so that when combined with the second part it is present within the disinfecting composition at a concentration ranging from about 0.001% to about 2.0% by weight.

16. The system of claim 10, wherein the acid is present in the second part in an amount so that when combined with the first part it is present within the disinfecting composition at a concentration ranging from about 0.001% to about 2.0% by weight.

17. The system of claim 10, wherein the acid is present in the second part in an amount so that when combined with the first part the pH of the disinfecting composition is from about 1 to about 4.

18. The system of claim 10, wherein both the first part and the second part are independently in the form of an aqueous solution, emulsion, microemulsion, cream, gel, solid block, tablet, powder, pellet, or prill.

* * * * *